(12) United States Patent
Warden et al.

(10) Patent No.: US 8,113,658 B2
(45) Date of Patent: Feb. 14, 2012

(54) OPHTHALMIC DIAGNOSTIC INSTRUMENT

(75) Inventors: Laurence Warden, Poway, CA (US);
Andreas W. Dreher, Escondido, CA (US); Gary D. Mills, Escondido, CA (US); Shui T. Lai, Encinitas, CA (US); William G. Foote, Poway, CA (US); David G. Sandler, San Diego, CA (US); Keith J. Dillon, La Jolla, CA (US)

(73) Assignee: Ophthonix, Inc., Vista, CA (US)

( * ) Notice: Subject to any disclaimer, the term of this patent is extended or adjusted under 35 U.S.C. 154(b) by 0 days.

(21) Appl. No.: 13/028,108

(22) Filed: Feb. 15, 2011

(65) Prior Publication Data

US 2011/0134389 A1    Jun. 9, 2011

Related U.S. Application Data

(62) Division of application No. 12/211,775, filed on Sep. 16, 2008, now Pat. No. 7,909,461, which is a division of application No. 10/971,769, filed on Oct. 22, 2004, now Pat. No. 7,425,067.

(60) Provisional application No. 60/581,127, filed on Jun. 18, 2004, provisional application No. 60/520,294, filed on Nov. 14, 2003.

(51) Int. Cl.
*A61B 3/10* (2006.01)

(52) U.S. Cl. .......................... 351/212; 351/216; 351/221

(58) Field of Classification Search ................... 351/205, 351/210, 211, 212, 216, 221, 246, 247

See application file for complete search history.

(56) References Cited

U.S. PATENT DOCUMENTS

| 5,777,718 | A  | * | 7/1998  | Kohayakawa ............... 351/211 |
| 5,963,300 | A  |   | 10/1999 | Horwitz |
| 6,781,681 | B2 |   | 8/2004  | Horwitz |
| 6,786,602 | B2 |   | 9/2004  | Abitbol |
| 6,899,428 | B2 | * | 5/2005  | Mihashi ....................... 351/239 |
| 7,293,873 | B2 |   | 11/2007 | Dai et al. |
| 2003/0071969 | A1 | | 4/2003  | Levine et al. |
| 2003/0214647 | A1 | | 11/2003 | Horwitz |
| 2004/0260275 | A1 | | 12/2004 | Liang et al. |

FOREIGN PATENT DOCUMENTS

EP          0 867 145          9/1998

OTHER PUBLICATIONS

Goodman, Introduction to Fourier Optics, McGraw Hill, Boston (1996).
Examiner's First Report for AU 2004291042, mailed Aug. 25, 2009, 3 pages.
Office Action for EP 04796887.0, mailed Oct. 21, 2010, 6 pages.

* cited by examiner

*Primary Examiner* — Huy K Mai

(74) *Attorney, Agent, or Firm* — Morrison & Foerster LLP

(57) ABSTRACT

A binocular wavefront measurement system for performing wavefront analysis on the eyes of a patient, the system comprising an optics system for providing an image to a first eye along a first optical path and an image to a second eye along a second optical path and a sensor system, said sensor system configurable in a first mode for performing a wavefront measurement of a first eye through a portion of the first optical path and configurable in a second mode for performing a wavefront measurement of a second eye through a portion of the second optical path.

22 Claims, 11 Drawing Sheets

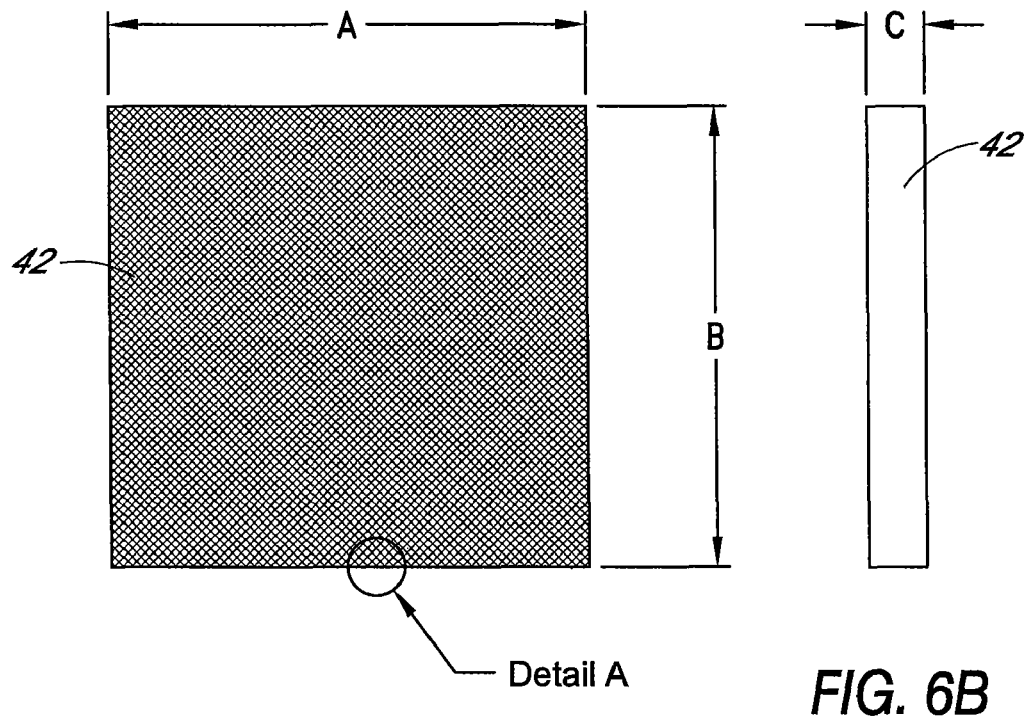
FIG. 6A
FIG. 6B
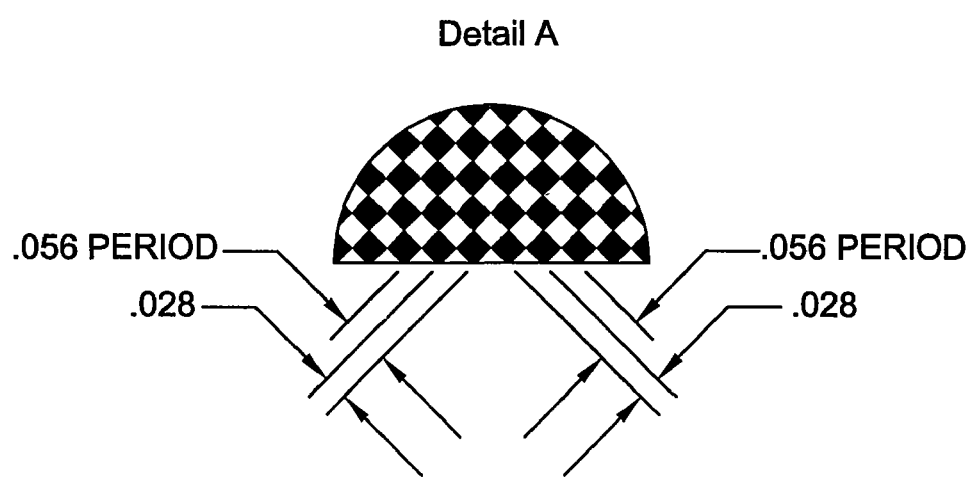
FIG. 6C

OPHTHALMIC DIAGNOSTIC INSTRUMENT

RELATED APPLICATIONS

This application is a divisional of U.S. Ser. No. 12/211,775, filed 16 Sep. 2008, which is a divisional of U.S. Ser. No. 10/971,769, filed 22 Oct. 2004, which claims priority to U.S. Ser. No. 60/581,127, filed 18 Jun. 2004, and U.S. Ser. No. 60/520,294 filed 14 Nov. 2003. The contents of these applications are hereby incorporated by reference in their entireties.

BACKGROUND OF THE INVENTION

1. Field of the Invention

This invention generally relates to systems and methods for performing measurements on an eye. More particularly, the invention relates to systems and methods for taking wavefront measurements of the eye.

2. Description of the Related Technology

One process for quantifying all the aberrations in the eye is known as wavefront analysis. Generally wavefront analysis involves illuminating an eye with a light beam, gathering light reflected from the eye and analyzing certain wavefront properties of the gathered light to determine aberrations in the eye. While an advantage of wavefront analysis is its ability to measure higher-order aberrations of the eye, measurement of the wavefront can be adversely affected in many ways, including, for example, accommodation state of the eye. When taking precise wavefront measurements of the eye, it is desirable that the subject's eye be stable, and in a natural, comfortable state, reducing or minimizing errors due to accommodation or eye movement. One way of ensuring the subject is comfortable and relaxed is to present an image to the eye which allows the subject to fixate on a specific object. When viewing this image, the subject's vision is preferably corrected to a level allowing them to fixate on the object. For example, the subject is preferably measured while viewing a natural scene at the desired distance for which the prescription will be generated. In an eye exam, this may mean viewing an eye chart or scene image placed at about sixteen feet or greater from the subject. However, a sixteen foot subject-to-object distance poses a problem for some exam areas due to space constraints.

Conventional wavefront measurement devices (examples including those available from Nidek, Tracy, and Wavefront Sciences) are monocular instruments. Some approaches to wavefront measurement employ the standard Shack-Hartmann sensor commonly used in ocular wavefront sensor devices. The Shack-Hartmann approach uses an optical element, such as a lenslet array, to divide the wavefronts from the aberrated pupil into smaller, non-overlapping sub-pupils, and forms in a common image plane the array of focused spots from all the subapertures. This approach is conceptually rooted in geometrical optics, and may suffer from well-known problems of dynamic range, limits to linearity, sub-aperture alignment issues, and increased complexity from large numbers of sub-apertures used to measure high-order aberrations beyond the common low-order Zernike modes. Another problem is that typical wavefront measurement systems require the patient to be rigidly restrained due to the length of time required for collection of the wavefront measurements. Such unnatural restraints add to the patient's discomfort and can result in increased eye movement as the discomfort increases. Additionally, using visible light for eye measurements also increases the patient's discomfort.

Another problem when determining visual acuity is that some patients, e.g., children or the elderly, may have a difficult time responding to vision tests that require the patient to make a subjective determination of which prescription produces the best vision for them. Improper responses by the patient can result in an inaccurate prescription and cause frustration in the patient and the operator administering the test. In addition, typically, wavefront systems require a skilled operator to properly position the patient and position the wavefront sensor in XYZ to get a "good" wavefront measurement. Factors which can cause erroneous results include, for example, improper XYZ positioning of the sensor, eye movement, tear film, eye blinks, eyelashes, glint, and spurious or uncontrolled accommodation. To effectively use wavefront systems and facilitate the widespread use of this technology, fewer burdens could be placed on the subjective actions of the operator and patient and more sophisticated techniques could be used to detect and control these factors. Typically, the operator must take multiple measurements and determine which measurements are valid for subsequent use. Certain methods for determining which images or processed results are similar and which outliers should be removed later could increase the effectiveness of the wavefront measurement process.

What is needed is a wavefront measurement system that overcomes one or more of the above-stated problems and other deficiencies in the art and that can be used over the widest possible patient population.

SUMMARY OF CERTAIN INVENTIVE ASPECTS

In one embodiment, the invention comprises a binocular wavefront measurement system for performing wavefront analysis on the eyes of a patient, comprising an optics system for providing an image to a first eye along a first optical path and an image to a second eye along a second optical path, and a sensor system, the sensor system configurable in a first mode for performing a wavefront measurement of a first eye through a portion of the first optical path and configurable in a second mode for performing a wavefront measurement of a second eye through a portion of the second optical path. The system can further comprise a stage system for positioning the sensor system to receive light from the first eye in the first mode and to receive light from the second eye in the second mode. In some embodiments the sensor system can be, e.g., a Hartman-Shack wavefront sensor or a ray tracing wavefront sensor.

In some embodiments the optics system can comprise a first internal target, a second internal target, and a path diverter with a first mode for positioning the first internal target in the first optical path and the second internal target in the second optical path, and with a second mode for positioning the first internal target out of the first optical path and the second internal target out of the second optical path, wherein the first and second optical paths extend to a location external to the binocular wavefront system when the optical path diverter is positioned in the first mode. In some embodiments, the first and second internal targets are a stereoscopic image pair. In other embodiments, the position of the first internal target and the second internal target is adjustable so as to stimulate an eye accommodation when viewing the first internal target and the second internal target through the binocular the visual optics system.

In another embodiment, the optics system of the binocular wavefront measurement system comprises a target light system for illuminating internal targets. In some embodiments the intensity of the illumination of the target light system can be controllable to provide variable illumination of the internal targets. In some embodiments the target light system provides illumination simulating one or more different lighting conditions, e.g., daylight, tungsten, fluorescent, moonlight, and/or night driving.

In another embodiment, the binocular wavefront measurement system further comprises a computer connected to the sensor system and the target light system, the computer configured to determine the diameter of a pupil of an eye and to control the intensity of the illumination of the light source based on the diameter of the pupil.

In another embodiment, a binocular wavefront measurement system for performing wavefront analysis on the eyes of a patient comprises prisms placed between the beam splitter and the patient's eye to simulate a specific convergence angle. For example, the binocular wavefront measurement system can comprise a convergence device located so as to provide an image from at least one of the first optical and second optical paths to at least one of the first and second eyes so as to invoke a convergence accommodation state of the eyes. In some embodiments, the convergence device comprises at least one low-angle prism.

In another embodiment of the binocular wavefront measurement system, the system comprises elements that compensate for aberrations present in the eyes of a patient. For example, the optics system can comprise a first set of optical elements configurable for controlling aberrations in a first eye, and a second set of optical elements configurable for controlling aberrations in a second eye. In another embodiment the optics system comprises at least one adaptive optics mirror having a movable mirror surface, the at least one adaptive optics mirror positioned in one of the first and second optical paths, and the at least one adaptive optics mirror being configurable for correcting an aberration by adjusting the movable mirror surface. In various embodiments the aberrations can comprise spherical, astigmatism, and/or coma.

In another embodiment, the sensor system of the binocular wavefront measurement system comprises a light source for emitting a light beam along a source optical path, an obstruction element having a blocking portion, the obstruction element disposed so as to position the blocking portion in the source optical path to obstruct a center portion of the light beam and produce an annular-shaped light beam for illuminating the retina of an eye, a modulation pattern element positioned in a path of a light beam reflected from the eye, and a sensor positioned to receive at least a portion of the light passing through the modulation pattern element so as to detect a wavefront aberration of the eye. In some embodiments the light source provides light having a beam diameter of about 2-3 mm in diameter. In some embodiments blocking portion of the obstruction element is about 1.5 to 2.5 mm in diameter. In some embodiments, the emitted light beam is a collimated light beam.

In another embodiment, the sensor system of the binocular wavefront measurement system comprises a light source providing light along a source optical path to an eye, the light source positioned relative to the eye such that light from the light source reflected from a retina of the eye travels in a first direction and light reflected from a cornea of the eye travels in a second direction, wherein the angle of the first direction relative to the source optical path is different from the angle of the second direction relative to the source optical path such that light traveling in the second direction does not enter an optical path for receiving light in the sensor system, a modulation pattern element positioned to receive light reflected in the first direction, and a sensor for detecting a wavefront aberration of the eye, the sensor positioned to receive at least a portion of light passing through the modulation pattern element. In some embodiments, the wavefront sensor system further comprises one or more optical elements positioned along the source optical path so as to decrease the spot diameter of the light at the retina of the eye. In various embodiments, the spot diameter of the light at the retina can be less than about 1 millimeter, less than about 600 micrometers, and/or less than about 400 micrometers.

The invention also comprises a method of detecting aberrations in the eyes of a patient, the method comprising positioning a binocular optics system relative to the eyes of a patient to provide an image to a first eye of a patient and an image to a second eye of a patient, positioning a wavefront sensor to receive light reflected from a retina of the first eye, illuminating the retina of the first eye with a light source, receiving the light reflected from the retina of the first eye in a detector while the patient is viewing the image with the first eye, and detecting a wavefront aberration of the first eye with the detector. In some embodiments, the method also can include controlling the binocular optics system to affect accommodation of the first and second eye. In some embodiments, the method comprises providing one or more aberrated images to the first eye of the patient and to the second eye of the patient. In various embodiments, providing one or more aberrated images invokes an accommodation state of the eye, which can include, for example, providing one or more aberrated images comprises providing images that invoke a distance accommodation state of the eyes, and/or providing one or more aberrated images comprises providing images that invoke a reading accommodation state of the eyes.

In other embodiments of the method of detecting aberrations in the eyes of a patient, the method comprises positioning the wavefront sensor to receive light reflected from a retina of the second eye, illuminating the retina of the second eye with the light source, receiving the light reflected from the second retina in the detector while the patient is viewing the image with the second eye, and detecting a wavefront aberration of the second eye with the detector.

Another embodiment of the invention comprises a method of identifying an aberration in an eye of a patient, the method comprising positioning a light source so as to emit a light beam along a source optical path, positioning an obstruction element having a blocking portion disposed in the source optical path so as to obstruct a center portion of the light beam and produce an annular-shaped light beam for illuminating the retina of an eye, illuminating the eye with the light source, receiving the light reflected from the retina in a detector, detecting a wavefront of the eye with the detector, and identifying an aberration in the eye based on the detected wavefront.

Another embodiment of the invention includes a method of measuring aberrations in at least one of the eyes of a patient by use of a wavefront sensor system comprising positioning a binocular optics system relative to the eyes such that a first eye is positioned in a first optical path of the binocular optics system and a second eye is positioned in a second optical path of the binocular optics system, positioning a light source relative to the first eye such that light from the light source that is reflected from a retina of the first eye travels in a first direction and light from the light source reflected from a cornea of the first eye travels in a second direction, wherein the angle of the first direction relative to the source optical path is different from the angle of the second direction relative to the source optical path such that light traveling in the second direction does not enter an optical path for receiving light in the sensor system, illuminating the retina of the first eye with the light source, receiving light reflected from the retina in a first direction through a portion of the first optical path, the light including a wavefront representing an aberration in the first eye, and identifying aberrations in the first eye based on the received wavefront.

In another embodiment of the invention, a method is disclosed of positioning a wavefront sensor, in a wavefront sensor system, for receiving light from an illuminated eye of a patient based on the location of a pupil of the eye, the method comprising illuminating the eye with a light source, positioning a wavefront sensor system in a first location relative to a pupil of an eye such that light reflected by the eye propagates along an optical path of the wavefront sensor for receiving light, detecting the light reflected by the eye in the wavefront sensor, determining the position of the pupil of the eye based on the detected light, and positioning the wavefront sensor in a second location relative to the pupil of the eye based on the determined position of the pupil, where the second location is a desired location for performing a wavefront measurement of the eye.

In yet another embodiment of the invention, a wavefront sensor system comprises a modulation element having a two-dimensional sinusoidal pattern positioned in a path of light to be analyzed, and a sensor system having a detector positioned to receive at least a portion of light passing through the modulation element, the detector being substantially located in a diffraction self-imaging plane relative to the modulation element and wherein the sensor system is capable of outputting a signal based on the light received by the detector. In another embodiment of the invention, a wavefront sensor system, comprises a modulation element having a two-dimensional checkerboard pattern positioned in a path of light to be analyzed, and a sensor system having a detector positioned to receive at least a portion of light passing through the modulation element, the detector being substantially located in a diffraction self-imaging plane relative to the modulation element and wherein the sensor system is capable of outputting a signal based on the light received by the detector.

In another embodiment, the invention comprises a method of determining aberrations in a reflective or internally reflective object system, comprising passing light reflected from an object system though a modulation element having a two-dimensional sinusoidal pattern so as to produce a near field diffraction pattern at a Talbot plane, detecting signals of the near field diffraction pattern at the Talbot plane, and using the detected signals to output a measure of an aberration in the object system.

In yet another embodiment, the invention comprises a method of determining an aberration in a reflective or internally reflective object system, comprising passing light reflected from an object system though a modulation element having a two-dimensional checkerboard pattern to produce a near field diffraction pattern at a Talbot plane, detecting signals of the near field diffraction pattern at the Talbot plane, and using the detected signals to output a measure of an aberration in the object system.

Another embodiment includes methods and systems of simulating light propagation through an eye. In one embodiment, the method comprises passing light through a lens disposed in front of a chamber, focusing the light on an imaging surface in the chamber by adjusting the distance between the lens and the imaging surface, rotating the imaging surface, and reflecting light from the imaging surface out of the chamber and through the lens. In another embodiment, the eye simulation system for testing wavefront sensor systems, comprises a housing having a chamber with an opening for allowing light to enter the chamber, a fluid located in the chamber, the fluid having a known index of refraction, a lens positioned relative to the housing such that light entering the opening of the chamber passes through the lens, and a rotatable imaging surface positioned in the chamber such that light passing through the lens propagates through the fluid and is incident on the rotatable imaging surface.

In still another embodiment, a pupilary distance is determined by a method of measuring the pupilary distance with a binocular wavefront measuring system, the method comprising aligning an optical path of a wavefront sensor system with a first pupil at a first position, analyzing light received from the first pupil by the wavefront sensor to determine position information of the first pupil relative to the first position, aligning the optical path of the wavefront sensor with a second pupil at a second position, analyzing light received from a second pupil by the wavefront sensor to determine position information of the second pupil relative to the second position, determining the pupilary distance based on the first and second position, and based on the position information of the first pupil relative to the first position and position information of the second pupil relative to the second position.

In still another embodiment, the invention includes a method of identifying aberrations of an eye of a patient comprising illuminating a first target with a light source configured to produce a first lighting condition, performing a first wavefront measurement of a pupil of a first eye of a patient while the first eye is viewing the first target illuminated with the light source configured to produce a first lighting condition, illuminating the first target with a light source configured to produce a second lighting condition, performing a second wavefront measurement of the pupil of the first eye while the first eye is viewing the first target illuminated with the light source configured to produce a second lighting condition; and determining the response of the pupil of the first eye to the second lighting condition based on the first and second wavefront measurements of the pupil of the second eye. In some embodiments, the method comprises illuminating a second target with a light source configured to produce a first lighting condition, performing a first wavefront measurement of a pupil of a second eye of a patient while the second eye is viewing the second target illuminated with the light source configured to produce a first lighting condition, illuminating the second target with a light source configured to produce a second lighting condition, performing a second wavefront measurement of the pupil of the second eye while the second eye is viewing the target illuminated with the light source configured to produce a second lighting condition, and determining the response of the pupil of the second to the second lighting condition based on the first and second wavefront measurements of the pupil of the second eye.

In another embodiment, a wavefront measuring system for determining a response of a pupil of an eye of a patient to a specific lighting condition comprises means for illuminating a first target with a light source configured to produce a first lighting condition, means for performing a first wavefront measurement of a pupil of a first eye of a patient while the first eye is viewing the first target illuminated with the light source configured to produce a first lighting condition, means for illuminating the first target with a light source configured to produce a second lighting condition, means for performing a second wavefront measurement of the pupil of the first eye while the first eye is viewing the first target illuminated with the light source configured to produce a second lighting condition, and means for determining the response of the pupil of the first eye to the second lighting condition based on the first and second wavefront measurements of the pupil. In some embodiments, the method also comprises means for illuminating a second target with a light source configured to produce a first lighting condition, means for performing a first wavefront measurement of a pupil of a second eye of a patient while the second eye is viewing the second target illuminated with the light source configured to produce a first lighting condition, means for illuminating the second target with a light source configured to produce a second lighting condition, means for performing a second wavefront measurement of the pupil of a second eye while the second eye is viewing the target illuminated with the light source configured to produce a second lighting condition, and means for determining the response of the pupil of the second eye to the second lighting condition based on the first and second wavefront measurements of the pupil.

Another embodiment includes a method of generating information for correcting optical aberrations for an eye of a patient, the method comprises positioning the eyes of the patient relative to a binocular visual optics system having a first optical path and a second optical path such that the line of sight of a first eye is aligned to the first optical path and the line of sight of a second eye is aligned to the second optical path, providing an image via the first optical path to the first eye and an image via the second optical path for the second eye; enabling a wavefront sensor to receive light reflected from the retina of the first eye, illuminating the retina of a first eye with a light source, receiving light reflected from the retina of the first eye at the wavefront sensor, measuring a wavefront aberration of the first eye from the light received from the first eye, identifying at least one optical aberration in the first eye based on the measured wavefront aberration, and generating information relating to the at least one optical aberration for use in a process to correct the at least one optical aberration of the first eye of the patient. In some embodiments, the process comprises generating a lens for correction of the identified optical aberration. In other embodiments, the process comprises changing an optical characteristic of the first or second eye through a surgical process to correct the identified optical aberration.

In another embodiment, the invention comprises a method of assessing the accommodative range of the eyes of a patient comprising providing a plurality of images to the eyes through a binocular optics system which invoke a plurality of accommodative states in the eyes, receiving wavefront signals representing at least one feature of the eyes at the invoked accommodative states, and from the wavefront signals, determining the accommodative range of the eyes based on the at least one of feature of the eyes at a plurality of invoked accommodative states.

In yet another embodiment, the invention comprises a method of providing controlled optically aberrated images to the eyes of a patient, the method comprising providing images through a binocular optics system to a first eye and a second eye, receiving wavefront signals representing at least one aberration in the first and second eyes, identifying an aberration of the first eye and an aberration of the second eye based on the wavefront signals, determining a correction for the identified aberration of the first eye and a correction for the identified aberration of the second eye, and adjusting the binocular optics system based on the determined corrections such that images provided to the eyes through the adjusted binocular optics system are optically compensated for the aberrations. In some embodiments, the aberrations comprise spherical, astigmatism, and/or coma.

In another embodiment, the invention comprises a system for providing a patient controlled optically aberrated images to the eyes of a patient comprising means for providing images through a binocular optics system to a first eye and a second eye, means for receiving wavefront signals representing at least one aberration in the first and second eyes, means for identifying an aberration of the first eye and an aberration of the second eye based on the wavefront signals, means for determining a correction for the identified aberration of the first eye and a correction for the identified aberration of the second eye, and means for adjusting the binocular optics system based on the determined corrections such that images provided to the eyes through the adjusted binocular optics system are optically compensated for the aberrations.

In yet another embodiment, the invention comprises a method of identifying aberrations in an eye of a patient, the method comprising positioning a binocular optics system relative to eyes of a patient such that a first eye is positioned along a first optical path of the binocular optics system and a second eye is positioned along a second optical path of the binocular optics system, receiving a first wavefront representing an aberration in the first eye through a portion of the first optical path, and identifying an aberration in the first eye based on the first wavefront received. In some embodiments, the method also comprise positioning a wavefront sensor in a first location to receive a first wavefront from the first eye through a portion of the first optical path, positioning the wavefront sensor in a second location to receive a second wavefront from the second eye through the second optical path, receiving a second wavefront representing an aberration in the second eye through a portion of the second optical path, and identifying an aberration in the second eye based on the second received wavefront.

In another embodiment, the invention comprises a method comprising analyzing an image in the first group of wavefront images to determine a first location of the pupil in the image, wherein the image was generated using a wavefront sensor located at a first position relative to the pupil, comparing the first location of the pupil to a predetermined location, and if the first location of the pupil is different from the predetermined location by a predetermined amount, moving the wavefront sensor to a second position relative to the pupil such that a subsequent image depicts the pupil at a second location wherein the second location of the pupil is closer to the predetermined location than the first location of the pupil. In some embodiments, the method also includes storing a plurality of wavefront images generated after the second wavefront image was generated, combining the stored images to form an averaged image, and determine a wavefront measurement from the averaged image. In other embodiments, the method further includes forming a set of wavefront measurements, each wavefront measurement being determined from an averaged image, comparing the set of wavefront measurements to identify anomalies in the plurality of wavefront measurements, and identifying one or more wavefront measurements in the set of wavefront measurements to provide for correcting aberrations in the object based on the identified anomalies.

BRIEF DESCRIPTION OF THE DRAWINGS

The above and other aspects, features, and advantages of the invention will be better understood by referring to the following detailed description, which should be read in conjunction with the accompanying drawings, in which:

FIG. 6A is an example of a two-dimensional x-y pattern used on a modulating element of a wavefront sensor.

FIG. 6B is a side view of a modulating element of a wavefront sensor.

FIG. 6C is illustrates an example of an x-y pattern used on a modulating element of a wavefront sensor.

DETAILED DESCRIPTION OF CERTAIN INVENTIVE EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention can include several novel features, no single one of which is solely responsible for its desirable attributes or which is essential to practicing the inventions herein described.

Figure 1A:
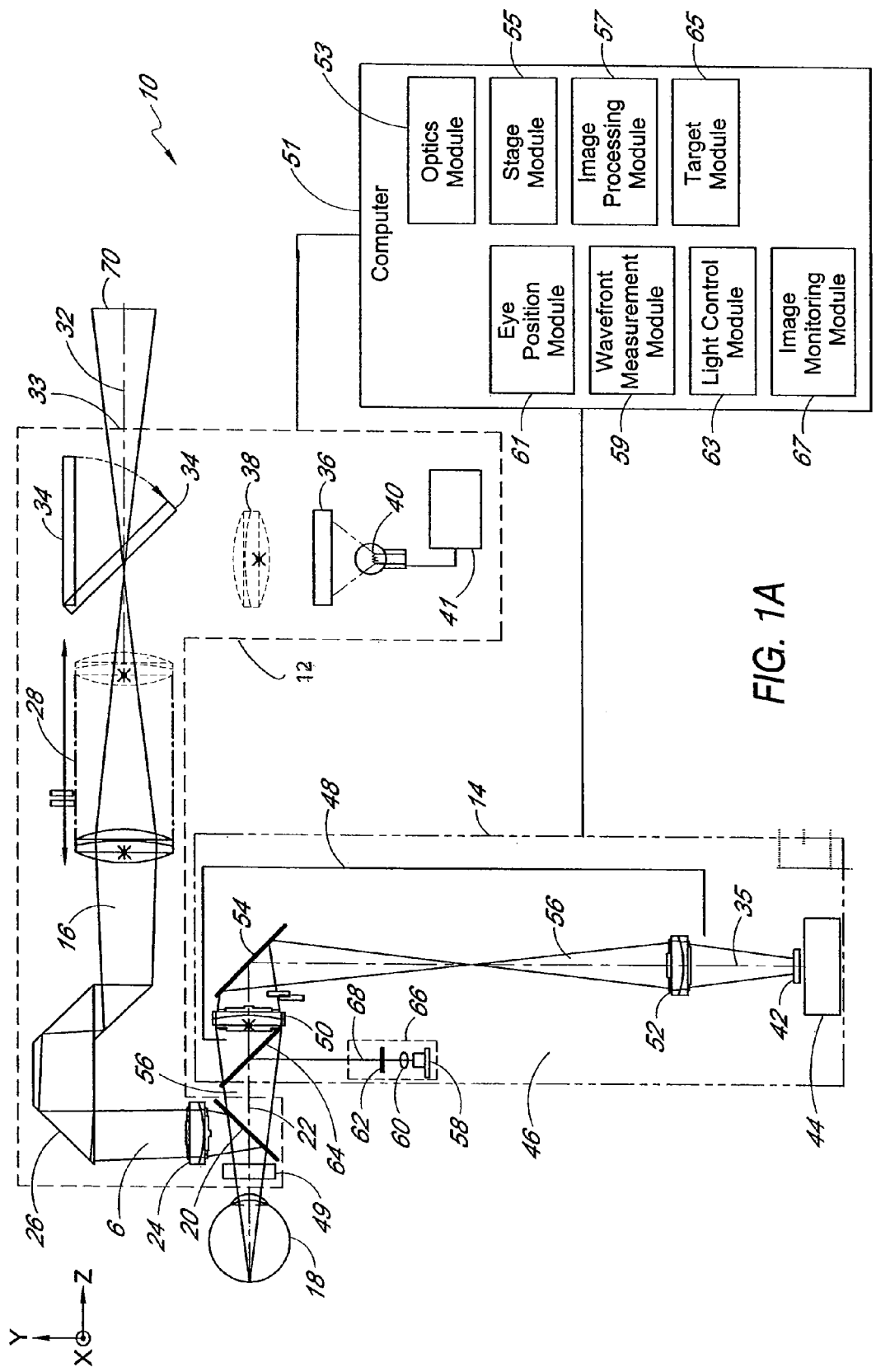
FIG. 1A is a schematic representation of an ophthalmic instrument.
Figure 1B:
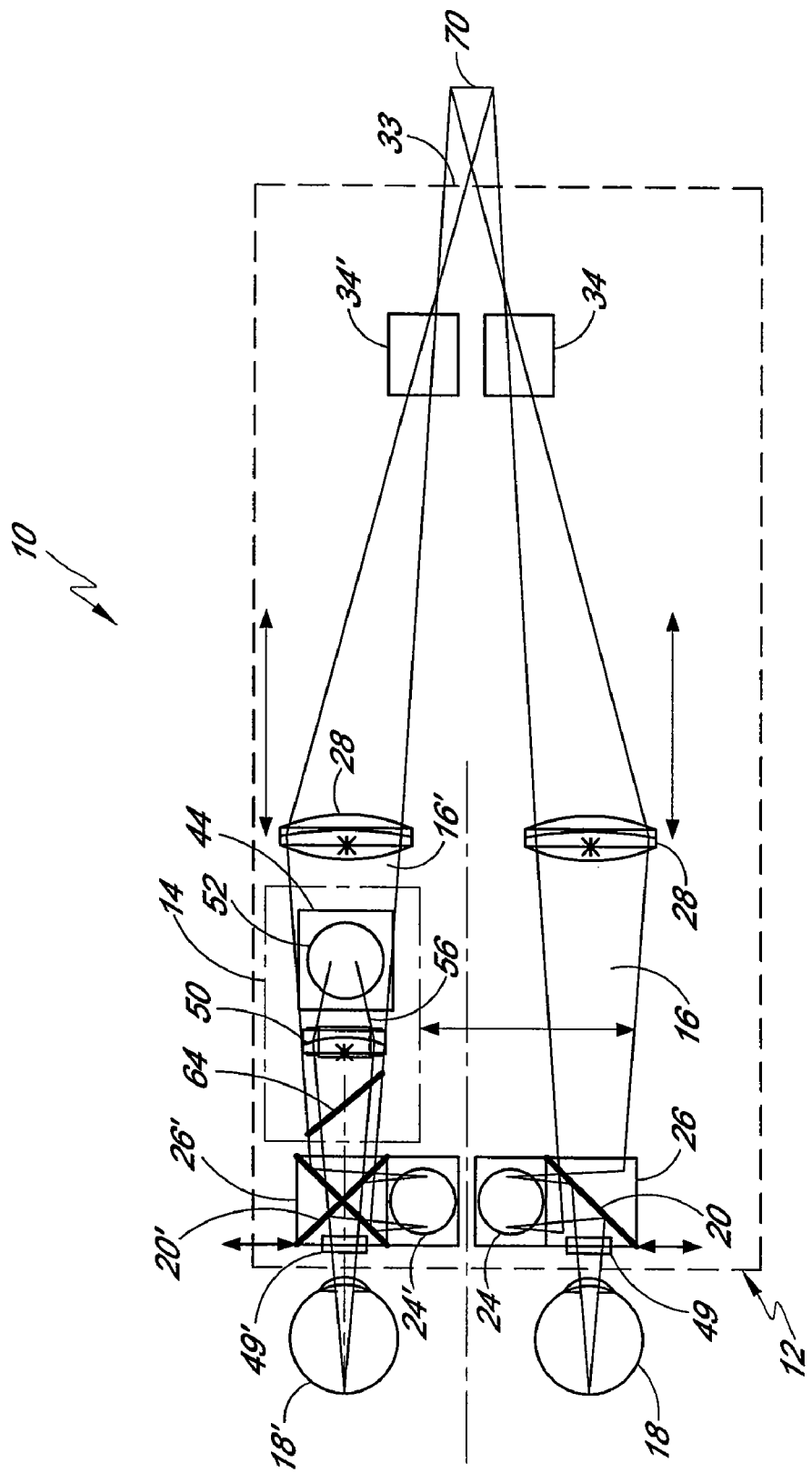
FIG. 1B is a top plan schematic representation of an ophthalmic instrument.

An embodiment of an ophthalmic instrument 10 shown in FIGS. 1A and 1B, and described herein can meet the requirements of an eye wavefront measuring system for use by eye care professionals, and at the same time be affordable so that it can be deployed in many thousands of OD and MD offices around the world. What has been a rather obscure technology in the hands of a few experts, can now be transformed into a widely used technology for the benefit of eye care. In particular, by keeping the instrument as simple as possible and carefully considering patient comfort issues, an embodiment of the instrument described herein is designed to be used over the widest possible patient population, including diagnosing vision problems and abnormalities in children.

The ophthalmic instrument 10 includes binocular visual optics 12 and a wavefront sensor assembly 14, according to one embodiment. Measurements of the eye taken under binocular conditions are preferred as being generally more accurate than those taken under monocular conditions. In some embodiments, the ophthalmic instrument 10 can also include a computer 51 connected to the visual optics 12 and/or the wavefront sensor assembly 14.

FIG. 1A shows a side view of the ophthalmic instrument 10 and a right visible optical path 16 from an object system (for example, an eye) 18 through the visual optics 12 to an external target 70. An "object system" as used herein refers to an object which can be aligned with a left and right optical path through the binocular visual optics 12. Once aligned, a wavefront measurement can be performed by the wavefront sensor assembly 14 when it is also aligned with a portion of the desired left or right optical path and the object. Generally herein, the object will be referred to as an eye, however, the "object" or "object system" should not be construed as being limited to an eye, as there are other types of suitable objects (for example a model eye or any other device that is suitable for wavefront measuring).

FIG. 1B shows a top plan view of the ophthalmic instrument 10 and shows the right visible optical path 16 for the right object system or eye 18 and a left visible optical path 16' for the left object system or eye 18'. The right visible optical path 16 and the left visible optical path 16' include similar optical elements and operate in a similar manner. Although only the right visible optical path 16 is shown in FIG. 1A and described, the description is similar for the left visible optical path 16'.

As in FIG. 1A, the visual optics 12 can include an infrared (IR)/Visible beamsplitter 20 disposed in front of the right eye 18. In this exemplary design, the IR/visible beamsplitter 20 has a surface oriented at about a 45° angle with respect to an optical axis 22 of the wavefront sensor assembly 14 when it is shown as aligned with the right eye 18. The reflective surface of the IR/visible beamsplitter 20 is disposed towards the right eye 18 along the right visible optical path 16 and reflects visible light to the right eye 18. The reflective surface of the IR/visible beamsplitter 20 is, however, substantially transparent to selected IR wavelengths that can be used in the ophthalmic instrument 10 to illuminate the eye 18 while conducting wavefront measurements. One or more prisms 49 are disposed in the right visible optical path between the eye 18 and the IR/Visible beamsplitter 20 for simulating convergence angles to objects (e.g., targets).

The visual optics 12 also includes a fixed lens 24, an inverting prism 26, and a movable lens assembly 28 disposed along the right visible optical path 16. The fixed lens 24 is disposed between the IR/visible beamsplitter 20 and the inverting prism 26, and focuses light from the inverting prism 26 so the eye 18 can perceive an image (e.g., of the external target 70) in the light reflecting from the IR/visible beamsplitter 20 and propagating into the right eye 18. The movable lens assembly 28 includes a set of one or more lenses that can be positioned along the visible optical path 16 for correcting errors (e.g., spherical) in the eye 18. The set of lenses can also be positioned to control eye accommodation, allowing an eye 18 to fixate on an object at a particular perceived distance and place its accommodation in a known state. In some embodiments, the movable lens assembly 28 includes a set of lenses (e.g., one or more lenses) to correct for astigmatism. In some embodiments the movable lens assembly 28 includes two cylinder lenses that can be used in conjunction with the spherical correction lens. The two cylinder lenses can have equal power and could be rotated independently about the visual optical axis 16 using either manually or using computer controlled motors, a computer 51 and an optics control module 53. In such an embodiment, if the eye 18 does not require astigmatism correction the two cylinder lenses can be positioned at 90 degrees to one another, which cancels the effect of each lens. To correct astigmatism in the eye, each lens can be positioned to a specified axis location with respect to each other resulting in astigmatism correction of a given power at the required axis. In other embodiments, the movable lens assembly 28 can include a spherical lens can be positioned off-axis from the main optical axis 32 for correction of coma. Visual optics 12 configured with a movable lens assembly 28 that includes one or more lenses for correction of astigmatism can be used as a phoroptor system. Configuring the movable lens assembly 28 with a lens or set of lenses for coma correction provides for correcting an eye 18 which cannot be achieved in a phoroptor. The inverting prism 26 includes a plurality of reflective surfaces arranged to invert and flip an image (e.g., rotate the image about orthogonal x- and y-axes in a plane perpendicular to an optical axis 32 through the visual optics path 16). In some embodiments, the inverting prism 26 can translate horizontally to accommodate various pupilary distances between the right and left eyes.

The visual optics 12 includes a path diverter 34 positioned between the movable lens assembly 28 and an opening 33 in the visual optics 12 through which a suitably positioned external target 70 can be seen in a patient's field of view. The path diverter 34 can be optionally positioned to intersect the visible optical path 16, diverting the subject's field-of-view such that the internal target 36 is included in the visible optical path 16. The path diverter 34 shown in FIG. 1A includes a mirror for diverting the field-of-view. In other embodiments, the path diverter can include other optical elements that change the visible optical path 16, for example, a prism or a beam splitter. The visual optics 12 can also include an internal target 36 and a target lens 38 disposed between the path diverter 34 and the internal target 36. The target lens 38 can be used to position an image of the internal target 36 at a desired perceived image distance as seen by the eye 18. In some embodiments, multiple targets (not shown) can be included in the visual optics 12 and placed at different distances, or different perceived distances, to present both near and far target images to the eye 18. The configuration of visual optics 12 can include a similar target lens 38 in the optical elements that define the left and right visible optical paths 16. Alternatively, the configuration of the visual optics 12 can include two different lenses 38 or sets of lenses of differing focal lengths in the optical elements that define the left and right visible optical paths 16 for generating different perceived distances for each eye 18. In some embodiments, the internal targets can be stereoscopic targets, providing a three-dimensional effect and visually reinforcing the desired perceived image depth.

The visual optics 12 can also include a target light source 40 that illuminates the internal target 36. This target light source 40 provides illumination of the internal target 36 using a variety of different types of light sources, according to various embodiments. For example, the target light source 40 can include a light emitting diode (LED), an incandescent light bulb, a fluorescent light bulb, and/or any other type of light source that can provide suitable illumination for the internal target 36 so that the eye 18 can perceive the internal target 36. In various embodiments, the target light source 40 is connected to a conventional light control electronics 41 which controls the intensity of the target light source 40. Furthermore, the light from the target light source 40 can be changed by the control system to allow for specific lighting conditions which represent real-world conditions such as night time driving, office or daylight.

In an alternative embodiment, an adaptive optics mirror (not shown) can be used in place of one of the surfaces of the image inverting prism 26 of the visual optics 12. In addition to providing movable spherical and astigmatic correction optics, an adaptive optics mirror can be used in the visible optical path 16 to provide a high-order correction (above focus and astigmatism). The adaptive optics mirror can be controlled through software based on measurements from the wavefront sensor assembly 14 in, for example, an iterative process. The adaptive optics mirror correct for aberrations in the eye 18, or it can be used in conjunction with focus and astigmatism correction lenses in the movable lens assembly to correct aberrations. Using spherical and astigmatic corrective lenses in conjunction with the adaptive optics mirror allows the use of a less expensive, shorter stroke adaptive optics mirror. A suitable adaptive optics mirror is available from Boston Micromachines Corporation, Watertown, Mass., and Flexible Optical B. V., Delft, The Netherlands.

Still referring to FIGS. 1A and 1B, the ophthalmic instrument 10 also includes a wavefront sensor assembly 14, such as, for example, a self imaging diffractive optic sensor, a Shack-Hartmann or ray tracing system. In one embodiment, the wavefront sensor assembly 14 includes illuminating optics 66 that provides a light beam along a right injection path 68 for illuminating the eye 18. The illuminating optics 66 includes an eye light source 58, which can be a variety of suitable light sources including a laser diode. In some embodiments, the light source 58 is an infrared light source, for example, an infrared laser diode or super luminescent diode ("SLD"), according to one embodiment. The illuminating optics 66 also includes a pin hole optical element 62 disposed along the injection path 68 along which light propagates from the eye light source 58 to the eye 18. The illuminating optics 66 can further include focusing optics 60 disposed along the injection path 66, between the pin hole 62 and the eye light source 58. The pin hole optical element 62 and focusing optics 60 are included in the illuminating optics 66 for some embodiments where the eye light source 58 is a SLD. In other embodiments, the illumination optics 66 can include various types of lasers as the eye light source 58. In various embodiments where the eye light source 58 is a laser, the laser can produce a narrow substantially collimated beam. In some embodiments, therefore, collimating optics such as a collimating lens may not be needed. Other types of an eye light source 58, including other types of light emitting diodes, can also be employed in the illuminating optics 66. In some embodiments where the eye light source 58 is a laser diode or SLD, the eye light source 58 is focused onto a fiberoptic and collimated into a small beam by a focusing lens (not shown). The output of the fiberoptic is coupled to a micro-lens which provides a small collimated beam to the eye.

The wavefront sensor assembly 14 also includes a beamsplitter 64 disposed in both the wavefront optical path 56 and in the injection path 68, and aligned along the optical axis 22 and positioned at a 45 degree angle with respect to the optical axis 22. In some embodiments, the beamsplitter 64 is a 90%/10% beamsplitter (referred to hereinafter as the "90/10 beamsplitter 64") that reflects 90% and transmits 10% of the light incident thereon. The 90/10 beamsplitter 64 is disposed such that a light beam from the eye light source 58 propagating from the illuminating optics along the injection path 68 to the 90/10 beamsplitter 64 reflects off the reflecting surface of the 90/10 beamsplitter 64 and propagates along the optical axis 22 of the wavefront sensor assembly 14 through the prism 44 and into the eye 18. Other combinations of pass to reject ratios can also be used besides 90/10 such as 80/20, 70/30, etc.

Preferably, the light beam directed into the eye 18 is substantially narrow. In various embodiments, the divergence of the beam propagating to the eye 18 is sufficiently small and the light beam is sufficiently narrow such that the cross-sectional dimensions (e.g., diameter or width) of the light beam as measured in a plane across the beam orthogonal to its direction of propagation towards the eye 18 are less than the size of the pupil of the eye 18. Preferably, the light beam entering the eye 18 has a cross-sectional dimension, such as diameter or width that is substantially less than the average diameter of the pupil. For example, the pupil is typically circular and has an average width of between about 4 to 8 millimeters, e.g., 6 millimeters. In various embodiments, the diameter of the light beam directed through the pupil is less than about 1 millimeter across and can be between about 200 to 600 micrometers (μm), e.g., about 400 μm. The light beam is preferably small to reduce the effect of an aberration of the eye 18 on the light beam. Also, the light beam is sufficiently small such that an aberration in the cornea of the eye 18 does not alter the light beam entering the eye 18 and does not increase the size or deform the shape of the light spot formed where the beam is incident on the retina. Preferably, the light spot formed on the retina is substantially small, (e.g., relative to the ocular lens and cornea) and approximates a point source.

Figure 10:
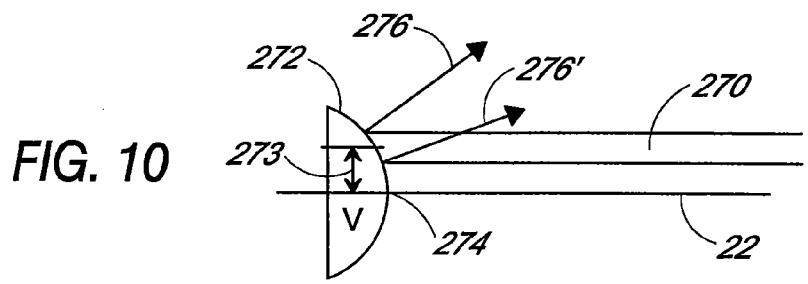
FIG. 10 is an illustration showing a light beam that is off-set from an optical axis incident on a pupil of an eye.

In various embodiments, the light beam from the illuminating optics 66 does not propagate along the optical axis 22, but instead is displaced from the optical axis 22. For example, as shown in FIG. 10, the center of a beam of light 270 propagating to the eye 18 is parallel to but laterally offset from the optical axis 22 of the wavefront sensor assembly 14. The center of the beam of light 270 is incident on the cornea 272 at an offset distance 273 from the vertex 274 of the cornea 272 (e.g., where the optical axis 22 intersects the cornea 272). As illustrated in FIG. 10, laterally offsetting the light beam incident on the eye 218 causes light reflected from the cornea 272 (represented by the reflected rays 276 276') to be directed at angles with respect to the optical axis 22. This results in a reduction in the reflected portion of the light beam 270 from the surface of the cornea 272 back along the optical axis 22 and through the wavefront optical path 56 to the wavefront sensor 44. Accordingly, the disruption of wavefront measurement caused by retro-reflected light from the cornea 272 is also reduced.

Figure 11:
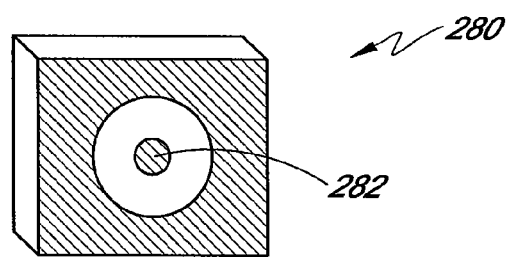
FIG. 11 is a perspective view of an optical element having a center obstruction.
Figure 12:
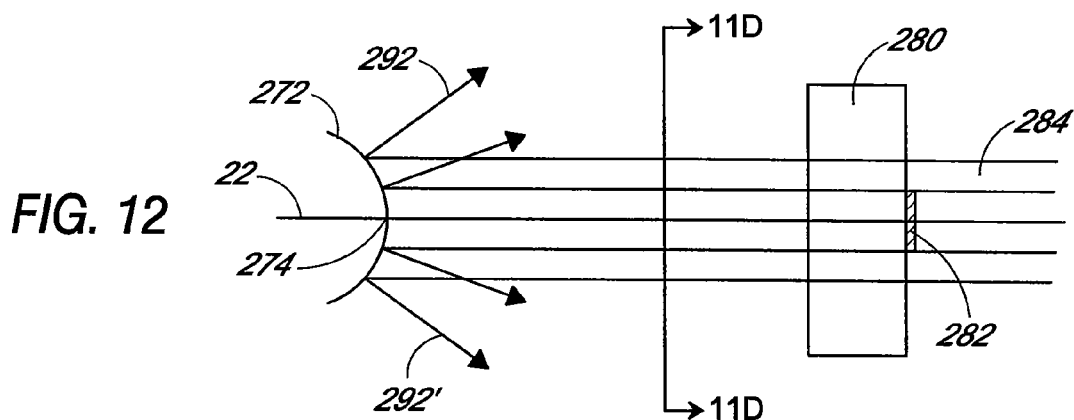
FIG. 12 is an illustration of the optical element of FIG. 11 placed in a beam of light incident on the pupil of the eye.
Figure 13:
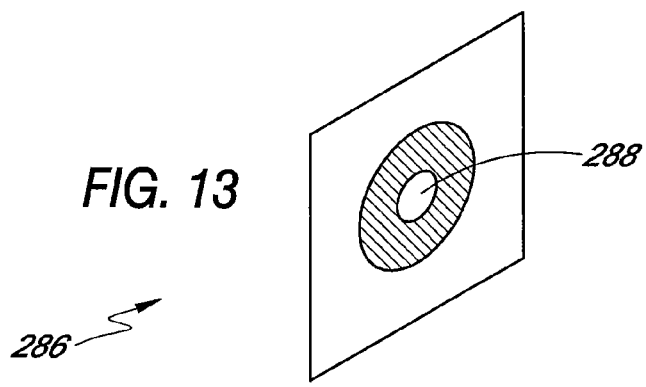
FIG. 13 is a perspective view representation of a cross-section of a beam of light formed by using the optical element shown in FIG. 11.

In some embodiments, the beam from the eye light source 58 is disposed directly down the optical axis 22 of the wavefront sensor assembly 14 and into the eye 18. An optical element 280 (FIGS. 11 and 12) having a central obstruction 282 can be inserted in the path of the beam 284 to produce a beam with an annular or doughnut-shaped cross-section 286 (FIG. 13) having a central obscuration 288. For example, the optical element 280 can be disposed in the injection path 68 between the illuminating optics 66 and the 90/10 beamsplitter 64 (FIG. 1A). The annular-shaped beam formed by optical element 280 can intersect regions of the cornea 290 off-center from the vertex 274 of the eye 18 and result in light being reflected from the cornea in directions other than back along the optical axis 22. This embodiment can increase the amount of light that could be injected into the eye 218, when compared to off-setting the incident beam as shown in FIG. 10, and reduce the portion of light reflected 292 by the cornea 290 along the optical axis 22 and directly into the wavefront sensor assembly 14 to also reduce retro-reflection disruptions of wavefront measurements. In some embodiments the beam can be 2-3 mm in diameter and have a blocking portion of 1.5 to 2.5 mm in diameter. The beam is preferentially collimated as presented to the eye. In yet another embodiment, the beam can be made to diverge or converge using one or more fixed or movable optics to compensate for spherical error of the subject eye, to minimize the spot diameter at the retina.

As illustrated in FIG. 1A, the wavefront sensor assembly 14 can also include an optical relay lens system 48 that propagates light emitted from the eye 18 to a modulation device 42 placed perpendicular to the optical axis 35. The optical relay system 48 is disposed as part of the wavefront optical path 56 such that light emitting from the eye 18 and passing through the 90/10 beamsplitter 64 enters the optical relay lens system 48 which then focuses this light on the modulation device 42. According to one embodiment, the relay lens system 48 includes two lenses 50, 52. One or more fold mirrors 54 disposed between the two lenses 50, 52 make the overall design of the wavefront sensor assembly 14 more compact.

The wavefront sensor assembly 14 employs one or more modulation devices 42 having a periodic pattern that is imaged at the self-image plane or Talbot plane. The principle of Talbot self-imaging is treated in references which teach interference and wave optics, e.g., Joseph W. Goodman, *Introduction to Fourier Optics*, The McGraw-Hill Companies, Inc. which are incorporated herein by reference. The wavefront sensor assembly 14 may exploit the pure Talbot effect in order to overcome the problems associated with Hartmann-Shack and other approaches. The Talbot effect is based on the fact that when certain periodic intensity modulation patterns are placed at the optical pupil of the system, the modulation pattern will reappear at a predictable longitudinal position (Talbot plane) along the propagation path. Thus, the pupil is "self imaged," and the modulation pattern can be recorded by a detector placed at the position of the Talbot plane. If the optical system contains wavefront aberrations, the modulation pattern will be distorted relative to the periodic modulation element. The distortions on the periodic "carrier" intensity pattern can be extracted through computer algorithms applied to the image intensity values. The computer algorithms incorporate on Fourier transformation of the image, and subsequent extraction of the aberration information from the carrier signal.

Figure 7:
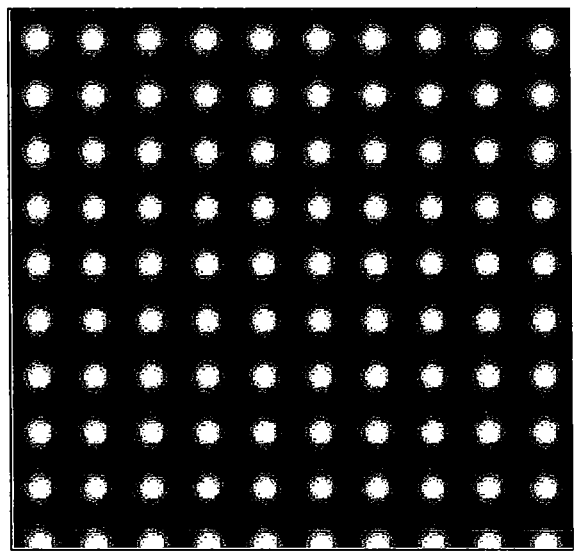
FIG. 7 is graphical example of a continuous two-dimensional sinusoidal function.
Figure 7:
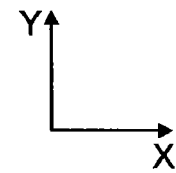

A sensor 44 is disposed at the self-image plane, or Talbot plane, of the modulation device 42. When the optical axis 22 of the wavefront sensor assembly 14 is aligned to the eye 18, and the eye 18 is illuminated by the illumination optics 66, light emitted from the eye 18 propagates along the optical axis 22, through the IR/visible beamsplitter 20 and the 90/10 beamsplitter 64, along the wavefront optical path 56, through the relay lens system 48 and the modulation device 42 to the sensor 44, which detects the light as modulated by the modulation device 42. A variety of suitable detectors can be used for the wavefront sensor 44, and the type of sensor 44 selected can depend on the type of light source 58 that is used. In some embodiments, the sensor 44 is a digital camera of suitable resolution and sensitivity. Sensors of various resolutions can be used and at least some over-sampling of the modulation pattern is preferred. In some embodiments, the resolution of the sensor is about four pixels per periodic element pitch. In some embodiments, a resolution of about eight pixels per periodic element pitch is preferred to ensure the pattern signal is over-sampled to improve immunity to noise. The modulation device 42 can include a two-dimensional pattern, e.g., a checkerboard pattern or a sinusoidal pattern, as discussed more fully below in reference to FIGS. 7 and 8, according to various embodiments.

Figure 2:
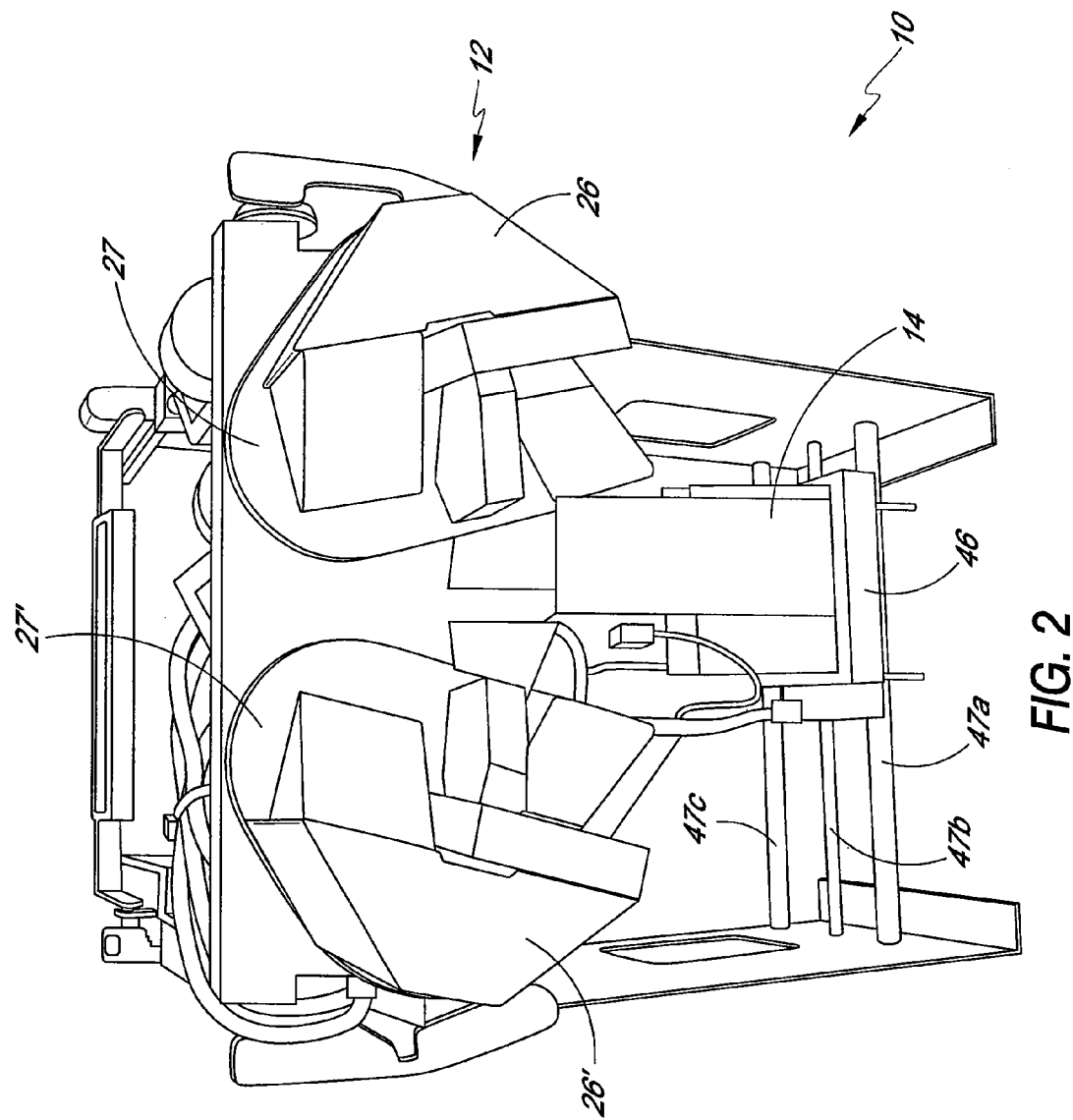
FIG. 2 is a perspective view of the visual optics of an ophthalmic instrument.
Figure 3:
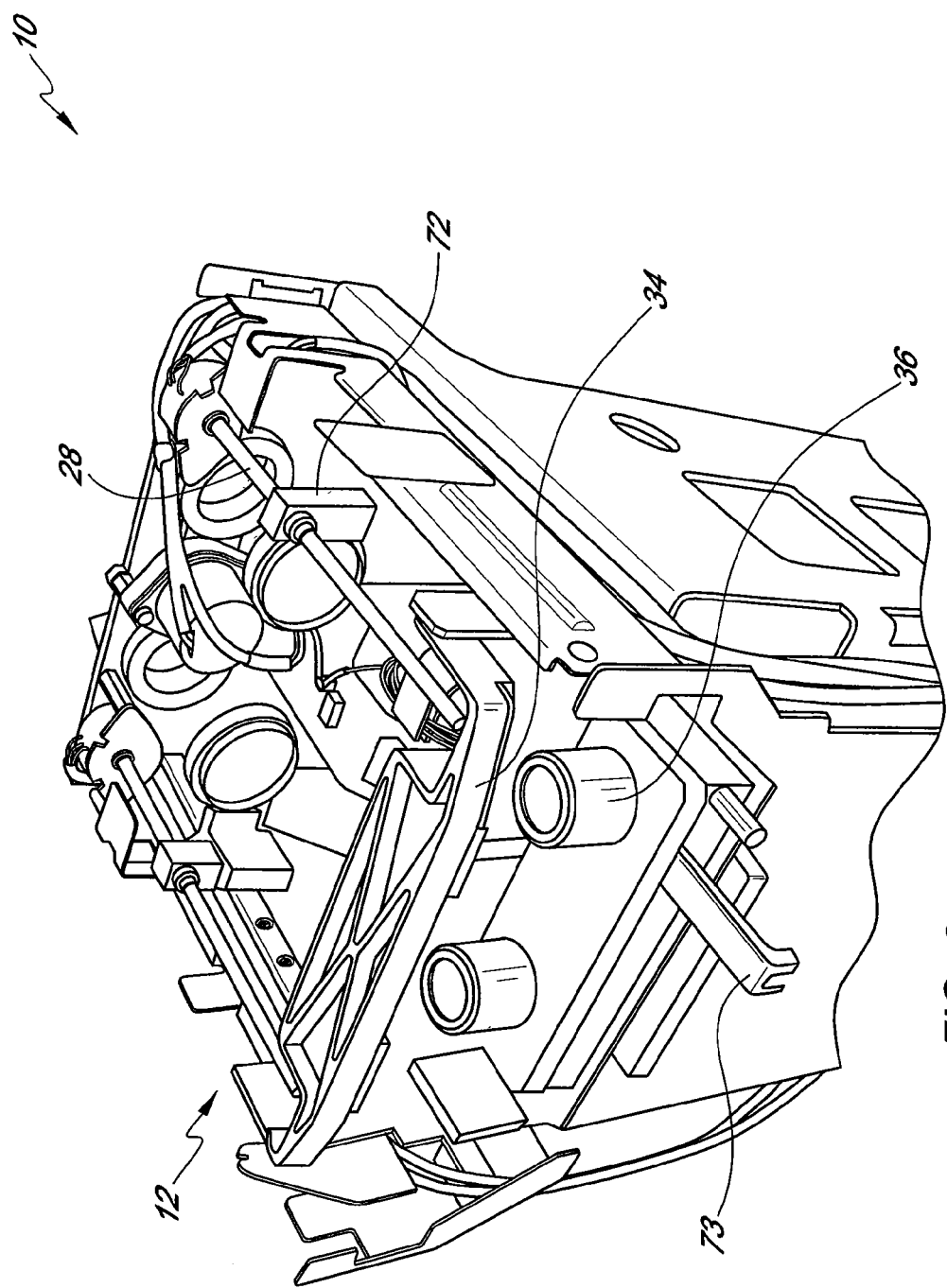
FIG. 3 is another perspective view of the visual optics of an ophthalmic instrument.

Perspective illustrations of an embodiment of the ophthalmic instrument 10 are shown in FIGS. 2 and 3, where FIG.

2 shows a perspective view of the front and FIG. 3 shows a perspective view of the back of the ophthalmic instrument 10. As shown in both FIGS. 2 and 3, the visual optics 12, which is also referred to as the visible look-through module, is disposed at the upper-end of the ophthalmic instrument 10. As shown in FIG. 2, the inverting prisms 26 are disposed on rotary bearings 27 to accommodate different pupilary distances between the eyes 18. The wavefront sensor assembly 14 is disposed on a stage 46 that can move on rails 47a, 47b, 47c to align with the right and left eye and their corresponding optics. FIG. 3 further illustrates an embodiment of the ophthalmic instrument 10 shown and described in FIGS. 1A and 1B. FIG. 3 shows, for example, the internal target 36, the flip-down path diverter 34, and the movable lens assembly 28 that includes a movable lens carriage 72.

Figure 4B:
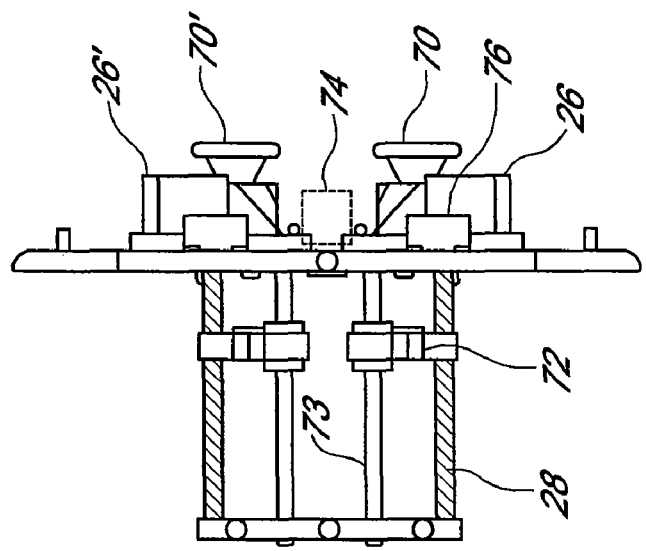
FIG. 4B is a side view of a portion of the visual optics of an ophthalmic instrument.
Figure 4A:
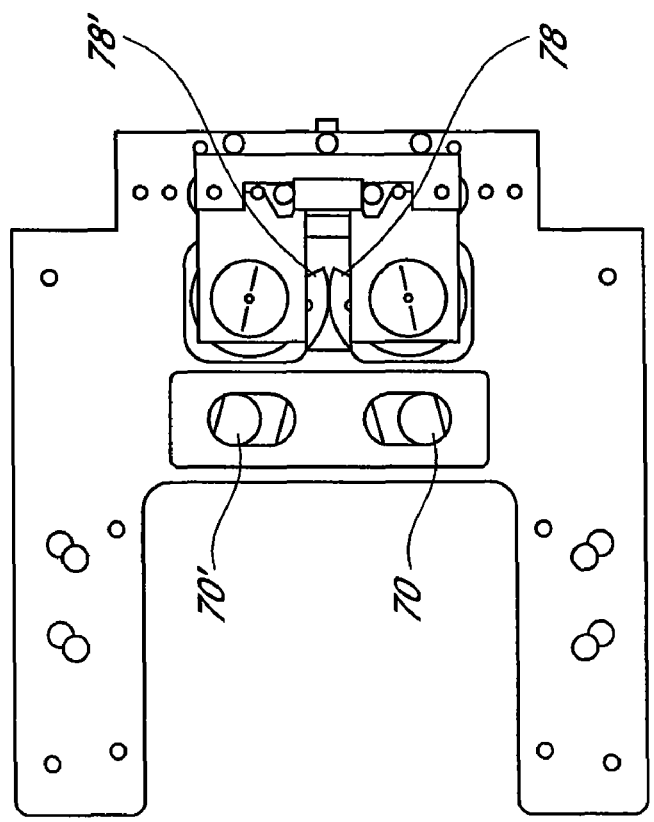
FIG. 4A is a front view of a portion of the visual optics of an ophthalmic instrument.

FIGS. 4A and 4B schematically illustrate front and top views of devices in the visual optics 12. As shown in these figures, the visual optics 12 includes oculars or eye optics 70 70' for the right and left eyes. The right and left image inverting prisms 26 26' can be connected by inverting prism linking gears 78 to control their movement in relation to each other. The wavefront sensor stage 46 (FIG. 2) can move in side-to-side translation to suitably align the wavefront sensor assembly 14 (FIG. 2) with the wavefront optical path 56 (FIG. 1) through the desired ocular 70 70' and when aligned, the visible optical path 16 (FIG. 1) and the wavefront optical path 56 (FIG. 1) can pass through these oculars 70 70'. The inverting prism 26 (FIG. 4B) is preferably rotatable about the optical axis 32 of the movable lens assembly 28 to accommodate for differing pupilary distances (e.g., the distance between the pupils of the eyes 18) in different patients. In some embodiments, a motor can drive the rotation of the inverting prism 26. The inverting prism 26, however, could alternatively translate horizontally (e.g., parallel to the x-axis) along with the movable lens to accommodate the subject's pupilary distance. The movable lens assembly 28 is preferably held by a movable mount that can be translated axially along the optical axis 32.

Referring to FIG. 4B, the distance between the oculars 70 can also be changed to accommodate different pupilary distances for different patients, according to some embodiments. A pupilary distance motor 74 can be used to move the oculars 70 70' horizontally to compensate for the patient's specific pupilary distance. The movable lens assembly 28 includes the movable lens carriage 72 that can hold a lens or a set of lenses. The movable lens carriage 72 can be translated axially along the optical axis 32 (FIG. 1A). In some embodiments, the position of the movable lens carriage 72 can be controlled by an optics control module 53 in the computer 51 (FIG. 1A). In some embodiments, one or both of the movable lens assemblies 28 can move in side-to-side translation to accommodate different pupilary distances, and in some embodiments the separation of the movable lens assemblies 28 are driven by a motor, and controlled either manually or can be controlled by an optics control module 53 in the computer 51 (FIG. 1A). In some embodiments, a motor can move the moveable lens carriage 72. For example, a lens motor 76 can be used to move the movable lens carriages 72 along a lens rail 73. One motor or numerous motors can be used to move the oculars 70 and the movable lens carriages 72. For example, in some embodiments each of the oculars 70 is moved by a separate motor (not shown), where this direction is preferably side-to-side along a plane perpendicular to the optical axis 22 (FIG. 1A). In some embodiments, a single motor can cause the varying separation between the oculars 70 and the movable lens carriages 72.

The angle between the optical paths 16 for the right and left eye can be changed as either one or both lens assemblies 28 are moved, according to some embodiments. In some embodiments, a low angle prism 49 (FIG. 1A) can be disposed in each of the visible optical paths 16 16' between the IR/visible beam splitters 20 20' and the patient's eyes 18 18'. Adjusting the position of the low angle prisms 49 modifies the gaze angle, or convergence, of the visible optical paths 16 16' to form a convergence angle matching a specific desired distance, for example reading distance of sixteen inches.

Referring again to FIG. 1A, in some embodiments, the wavefront sensor assembly 14 can be mounted on a movable XYZ stage 46 for three-dimensional positioning of the wavefront sensor assembly 14 with either the left or right eye of the patient. In some embodiments, the three-dimensional positioning of the wavefront sensor assembly 14 is controlled by a stage control module 55 in the computer 51. In these embodiments, the stage control module 55 receives positioning data either from a user or from other software, e.g., a pupil tracking module or an image processing module, and controls the XYZ stage 46 to position the wavefront sensor assembly to measure the left or right eye as the patient views a target through the visual optics 12. For example, an image processing module 57 can be included in the computer 51 for determining the edge, the center, and the size of the pupil of an eye. Based on this actual pupil location information, the stage control module 55 can position the wavefront sensor assembly 14 so that the pupil is in the desired XY location (e.g., centered in the image frame). In some embodiments, the stage can be automatically positioned in the Z direction to focus the image of the pupil, as described below for FIG. 14. In other embodiments, the XYZ stage 46 can be manually adjusted to position the wavefront sensor assembly 14 in three-dimensions (XYZ). The effect of different lighting conditions on the dilation of the pupil can also be determined using the image processing module 57. For example, the size (e.g., diameter) of the pupil can be measured and analyzed while subjecting it to various levels of illumination from the target light source 40, and the size of the pupil can be determined for each of the various levels of illumination.

Still referring to FIG. 1A, to determine a wavefront measurement of the eye 18, the illuminating optics 66 of the wavefront sensor assembly 14 provides a light beam along the injection path 68 that reflects off the 90/10 beamsplitter and enters the eye 18. Some of the light that enters the eye 18 reflects or scatters off the retina and is emitted from the eye 18. A portion of the emitted light propagates to the wavefront sensor assembly 14 along the direction of the optical axis 22, propagates through the IR/visible beamsplitter 20 and the 90/10 beamsplitter 64, propagates along the wavefront optical path 56, through the modulation pattern element 42 and falls incident on sensor 44. The sensor 44 detects the incident light and can provide related data to the incident light to the connected computer 51, which uses a wavefront analysis module 59 in the computer 51 to determine aberrations based on the wavefront measurement.

While taking wavefront measurements of an eye 18, various adjustments can be made in the visual optics 12 to change the eye's accommodation state such that specific wavefront measurements can be made at selected eye accommodation states and pupil states. For example, the illumination of the target perceived by the patient's eyes can influence the size of a patient's pupil. The intensity of the illumination for the target light source 40 can be controlled to light the internal target 36 at predetermined illumination. In some embodiments, the light source 40 can be controlled to illuminate the internal target 36 with light that simulates a particular environment by changing the light's chromaticity and/or intensity, for example, to simulate indoor lighting, outdoor natural lighting, office lighting, nighttime lighting, and/or night driving lighting conditions. To determine the reaction of the pupil to various lighting conditions, the wavefront sensor assembly 14 can measure the pupil at desired illumination levels and image processing software 57 can determine the resulting size of the pupil. The size of the pupil can be correlated with the illumination used to view the target 36 while measuring the pupil to determine the reaction of the pupil to the various lighting conditions.

Wavefront measurements of the eye 18 can be made when the eye 18 perceives either the external target 70 or the internal target 36. One mode, e.g., the "external target" mode, of the ophthalmic instrument 10 directs a subject's vision through the movable lens assembly 28 to the external target 70 located a distance away from the ophthalmic instrument 10, for example, at about sixteen feet away. The movable lens assembly 28 can be configured with suitable optical elements to correct the subject's vision so that the subject can reasonably view the external target 70. For example, the movable lens assembly 28 can include optics for correcting spherical, astigmatism, and coma aberrations. For this external target mode, the path diverter 34 rotates or moves out of the field of view of the visible optical path 16 allowing the eye 18 to view the external target 70 through the visual optics 12. The ophthalmic instrument 10 can also provide another mode, e.g., the "internal target" mode, for the subject to view the internal target 36. In the internal target mode, the path diverter 34 is rotated or moved into the field of view of the patient such that it intersects visible optical path 16, directing the visible optical path 16 vision to the internal target 36. The internal target mode is useful in small rooms where, e.g., there is not enough space for a sixteen foot distance to an external target. Accordingly, various embodiments of the visual optics 12 can be designed to include using the external target 70 and/or the internal target 36.

FIG. 1A shows the right visible optical path 16 of the visual optics 12 and its corresponding optical elements. FIG. 1A also shows the path diverter 34 can be disposed in the visual optics 12 between the movable lens assembly 28 and an opening 33 in the visual optics 12. The path diverter 34 can be moved into and out of the visible optical path 16, for example, by pivoting, rotating or sliding the path diverter 34. In some embodiments, when moved into the visible optical path 16, the path diverter 34 redirects the patient's vision onto the pair of internal fixation targets 36. Two sets internal targets are preferably built into the visual optics 12, one presenting an image at a simulated reading distance and the other at a relatively farther distance. In some embodiments, the path diverter 34 and targets 36 are actuated by a three-position lever 73 (FIG. 3). In the first position, the path diverter 34 is up allowing the subject to see external target 70 out the back of the ophthalmic instrument 10. In the second position, the path diverter 34 is lowered and a target or a set of targets 36 is displayed at a specified distance to the target position lens 38 for reading at 12 inches. In the third position, the path diverter 34 is still down and a second target or a set of targets is displayed at a predetermined perceived distance, for example, at about 16 feet. With the path diverter 34 rotated out of the visible optical path 16, the patient can look through the visual optics 12 at a real target 70 located at a relatively far distance. In some embodiments, a computer controlled actuator can position the path diverter 34 to display the desired targets or set of targets to the patient. Such an actuator can be controlled through software, e.g., a target control module 65, running on the computer 51. In some embodiments, the distance between the internal targets is adjustable, either manually or through a control mechanism to stimulate an eye accommodation when viewing the first internal target and the second internal target through the binocular the visual optics system. For example, the target control module 65 can be configured to control the distance between the first internal target and the second internal target to invoke a desired eye accommodation.

In another embodiment, the path diverter 34 can be used to provide a single target in a field-of-view that is shared between the two eyes. When a single target is used, one or more prisms 49 can be positioned in the visual optics 12 visible optical path 16 between the eye 18 and beamsplitter 20 to converge the images from each eye at a distance simulating the convergence angles for near and/or far targets. The flexibility of the visual optics path 16 allows the patient to look at a target after pre-correction for measured focus. The ophthalmic instrument 10 can include flexibility in OD or MD protocol, near vs. far, fogging vs. internal focusing, pre-corrected or uncorrected, and other combinations that can be desirable to use during measurement of the eye 18.

Measurements of a patient's right and left eyes can be made with the ophthalmic instrument 10 while the patient is viewing internal or external targets using the visual optics 12. The XYZ sensor stage 46 positions the wavefront sensor assembly 14 such that it can obtain a wavefront measurement of the desired eye. In one position, for example, the XYZ sensor stage 46 positions the wavefront sensor assembly 14 such that it aligns with the right eye and can obtain a wavefront measurement of right eye. The XYZ sensor stage 46 can move the wavefront sensor assembly 14 to another location such that the wavefront sensor assembly 14 is aligned with and can obtain a wavefront measurement of the left eye. The wavefront sensor stage 46 can move the wavefront sensor assembly 14 in three dimensions allowing it to line up the left or right eye with the wavefront optical path 56, on the optical axis 22. Additionally, the sensor stage 46 moves the wavefront assembly 14 from one eye to the other. If a computer 51 is used to control the position of the wavefront sensor stage 46, an eye position module 61 can be used to analyze the position of the eye 18 with respect to the wavefront sensor assembly 14 and provide information for moving the wavefront sensor stage 46 so as to align the wavefront sensor assembly 14 with the optical center of each eye 18.

Referring to FIG. 1A, when a patient is viewing a target through the visual optics 12, an optical element (e.g., a lens or set of lenses) in the moveable lens assembly 28 can be moved to a position along the visible optical path 16 to provide spherical correction for the eye. The inverting prism 26 flips the image of the target left to right and top to bottom so that the patient can see the target at its proper orientation. The movable lens assembly 28 can also include a plurality of lenses and other optical elements. For example, the movable lens assembly 28 can include two movable and rotating cylinder lenses to provide both spherical and astigmatic correction. The movable lens assembly 28 can include a plurality of refractive optical elements or other optics that includes correction for other high order aberrations as well, such as a spherical lens (not shown) positioned off-axis from the main optical axis 32 for correcting coma. For the majority of patients, spherical correction is sufficient to allow the patient to sufficiently fixate on the external target 70 and/or the internal target 36 while making a wavefront measurement.

One embodiment of the ophthalmic instrument 10 includes six motors for positioning the optics and the stage 46 (FIG. 2). In this example of a six motor embodiment, one pair of motors (not shown) can move the lens carriages 72 72' of the movable lens assemblies 28 28' (FIG. 4B), the pupilary distance motor (74) (FIG. 4B), rotates the inverting prisms 26, 26' to control the pupilary distance, and three motors (not shown) control the movement of XYZ stage 46 in three-dimensions. In another embodiment, four additional motors can be used to move optical elements to correct astigmatism. A plurality of sensors can be employed in the ophthalmic instrument 10 to provide feedback for positioning the optical elements of the movable lens assemblies 28, the XYZ stage 46, and/or the targets 36.

Referring to FIG. 1A, embodiments of the ophthalmic instrument 10 can include a computer 51 that can be configured with software for controlling the functionality of the ophthalmic instrument 10 and analyzing the wavefront measurement data. The computer 51 is in data communication with the wavefront assembly 14 and the visual optics 12 for sending and receiving data, signals and information relating to, for example, wavefront images, optics, stage position, image processing internal and external targets, eye position, wavefront measurement, lighting, image monitoring, and other data related to or controlling the process of obtaining wavefront measurements.

Figure 5:
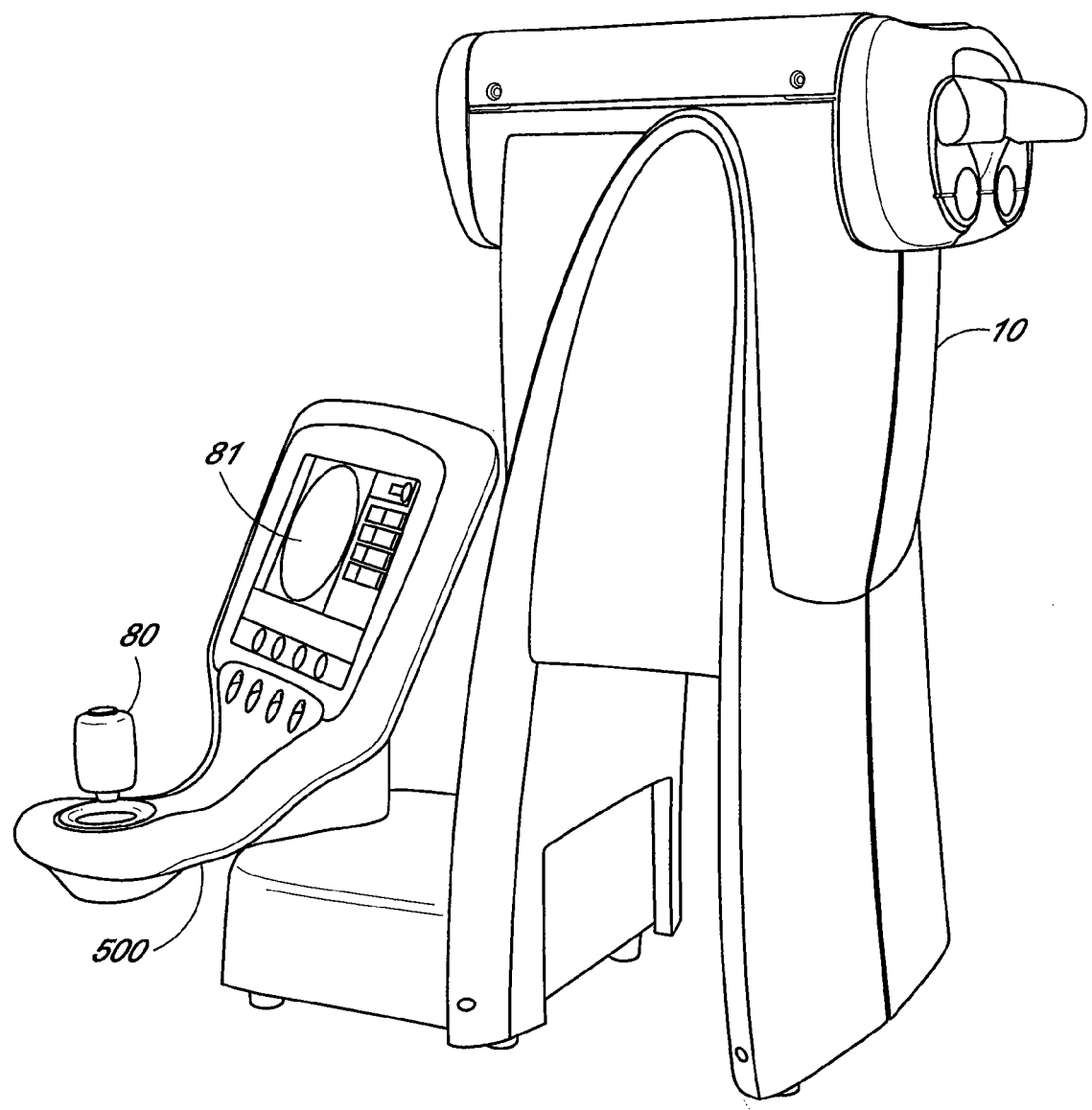
FIG. 5 is a perspective view of an ophthalmic instrument showing a joystick control system.

The computer 51 can be any suitable data processor controlled device, e.g., a Pentium-based personal computer, and can include one or more electronics control circuit boards and software modules which implement the motion control of lens and stage positioning motors, on/off and intensity control of the target light source 40 and the eye light source 58, as well as sensors located throughout the ophthalmic instrument 10. In one embodiment, the ophthalmic instrument 10 includes a computer 51 which includes an optics positioning module 53, a stage positioning module 55, an image processing module 57, a wavefront measuring module 59, an eye positioning module 61, a light control module 63, a target module 65, and a image monitoring module 67. In other embodiments, the computer 51 can have fewer or additional modules. The computer 51 can further include one or more input devices such as a keyboard, mouse, touch pad, joystick, pen-input-pad, camera, video camera and the like. The computer 51 can also include an output device, such as a visual display and an audio output. In some embodiments the visual display can be a computer display or the display 81 on control system 500 (FIG. 5).

Additionally, the computer 51 can include an addressable storage medium or computer accessible medium, such as random access memory (RAM), an electronically erasable programmable read-only memory (EEPROM), programmable read-only memory (PROM), erasable programmable read-only memory (EPROM), hard disks, floppy disks, laser disk players, digital video devices, compact disks, video tapes, audio tapes, magnetic recording tracks, electronic networks, and other devices to transmit or store electronic content such as, by way of example, programs and data. In one embodiment, the computer 51 is equipped with a network communication device such as a network interface card, a modem, or other network connection device suitable for connecting to a communication network and providing electronic information from the ophthalmic instrument 10 to another device. Furthermore, the computer 51 can execute an appropriate operating system such as Linux, Unix, Microsoft Windows, Apple MacOS, IBM OS/2 or other operating system. The appropriate operating system can include a communications protocol implementation that handles all incoming and outgoing message traffic passed over a network. In other embodiments, while the operating system may differ depending on the type of computer, the operating system will continue to provide the appropriate communications protocols to establish communication links with a network.

The modules included in the computer 51 can include one or more subsystems or modules. As can be appreciated by a skilled technologist, each of the modules can be implemented in hardware or software, and comprise various subroutines, procedures, definitional statements, and macros that perform certain tasks. Therefore, the description of each of the modules is used for convenience to describe the functionality of the computer 51 in the ophthalmic instrument 10. In a software implementation, all the modules are typically separately compiled and linked into a single executable program. The processes that are undergone by each of the modules can be arbitrarily redistributed to one of the other modules, combined together in a single module, or made available in, for example, a shareable dynamic link library. These modules can be configured to reside on the addressable storage medium and configured to execute on one or more processors. Thus, a module can include, by way of example, other subsystems, components, such as software components, object-oriented software components, class components and task components, processes, functions, attributes, procedures, subroutines, segments of program code, drivers, firmware, microcode, circuitry, data, databases, data structures, tables, arrays, and variables.

The various components of the computer 51 can communicate with each other and other components through mechanisms such as, by way of example, interprocess communication, remote procedure call, distributed object interfaces, and other various program interfaces. Furthermore, the functionality provided for in the components, modules, subsystems and databases can be combined into fewer components, modules, subsystems or databases or further separated into additional components, modules, subsystems or databases. Additionally, the components, modules, subsystems and databases can be implemented to execute on one or more computers 51.

FIG. 5 illustrates an embodiment of the housing for a control system 500 for the ophthalmic instrument 10. The control system 500 is used for interacting with the computer 51 (FIG. 1A) to position the wavefront sensor assembly 14, where positioning using the control system 500 is via a fly-by-wire joystick 80 similar to a video game. The joystick 80 can control three motors, giving the three degrees of freedom required for moving the wavefront sensor 14 between the left and right eye and aligning the wavefront sensor 14 with each eye 18. As shown in FIG. 5, the ophthalmic instrument 10 can be designed with the ergonomics of the patient and operator in mind, which can also help relax the patient. The ophthalmic instrument 10 also can include a display screen 81 that can be used, for example, for displaying the pupil and/or results of wavefront measurements. In other embodiments, the wavefront sensor 14 (e.g., FIG. 2) can be positioned using computerized, microprocessor or electronically controlled systems, for example, the computer 51.

As shown in FIG. 1A, the wavefront sensor assembly 14 can include one or more modulation device 42, which can also be referred to as a modulating element. The modulation device 42 can have periodic features that produce a self-image at the self-image or Talbot plane from light passing through the modulation element 42. The aberrations in the eye 18, in particular on cornea and the lens, are encoded in the self-image of the modulation device 42, and recorded by the sensor 44 (FIG. 1A). The sensor 44 can be, for example, a CMOS sensor the same as those used in digital cameras. The aberration information in the recorded image can then be extracted through Fourier-transform based algorithms performed by the computer 51. In various embodiments, the modulation device 42 can include one or more gratings, or the modulation device 42 can be configured on an element through which light suitably passes. In some embodiments, the modulation device 42 can include a fine-pitched two-dimensional repetitive x-y pattern.

One example of a pattern 42 is shown in FIGS. 6A-6C. FIG. 6A shows the view of a modulation device 42 that can be positioned perpendicular to and in the wavefront optical path 56, according to one embodiment. FIG. 6B shows a side view of the modulation device 42. The modulation device 42 includes periodic features that modulate a wavefront that was generated from light emitted from the eye 18 and propagating through the wavefront optical path 56 to the modulation device 42. FIG. 6C shows a detailed view of Detail A of FIG. 6A. In one embodiment, the dimensions (A and B of FIG. 6A) of the modulation device are about 1 cm×1 cm and represent the size of the image area of the camera plus a buffer area of about 2 mm on each side. The modulated wavefront propagates a few millimeters along the wavefront optical path 56 where an image of the element with periodic features is self-imaged and is detected by sensor 44 (FIG. 1A). Embodiments of sensor 44 that detect images at the self-image or Talbot plane are disclosed in U.S. patent application Ser. No. 10/014,037 entitled "Systems and Methods for Wavefront Measurement" filed Dec. 10, 2001, U.S. patent application Ser. No. 10/314,906 entitled "Systems and Methods for Wavefront Measurement" filed Dec. 9, 2002, which are each incorporated herein by reference in their entirety.

The wavefront sensor assembly 14 can provide very high-resolution wavefront information, for example, with greater than 300×300 measurement points across a 4 mm pupil. Information can be obtained that is far beyond the usual Zernike mode description and suitable for relatively smooth phase errors. The wavefront sensor assembly 14 preferably offers enough resolution to measure relatively sharp phase errors within the pupil and can handle high-frequency wavefront errors that might occur from prior surgical procedures. After the wavefront data is captured and analyzed, the wavefront analysis results may be displayed on a screen near the device, for example screen 81 of the joystick control system 500 (FIG. 5) or on a computer display device. The results can also be encoded into barcode format or transferred to another location via electronic means such as through the internet. The wavefront or Zernike data can be encoded in a barcode along with the other information such as, e.g., patient ID, left/right eye, and can be sent to a lab and used in the manufacturing of a lens which can include wavefront corrective elements.

During an exam using the ophthalmic instrument 10, a sequence of short exposures is preferably taken at one setting, which involves only one initial alignment of the patient. The captured images are preferably pre-screened for artifacts that can be the result of high frequency noise caused by, for example undesirable reflections from the eye, and processed. In this process, the patient is in the chair for only a few minutes, and the results can be ready to display to the operator in less than one minute. Since the measurement is fast, there is no need for rigid restraint on the patient during the eye exam. The comfort level of the patient is enhanced through the use of the invisible near-infrared laser as the eye light source 58. In one embodiment, the near-infrared laser can have a wavelength of about 850 nm. Due to the efficiency of the optical measurement of the wavefront sensor assembly 14, a light beam of substantially lower power can be used to illuminate the retina. The power, for example, may be lower by a factor of approximately 4-7 compared to other conventional wavefront instruments. Using infrared light in combination with the lower illumination power level increases the patient's comfort and safety.

In various embodiments of the invention, an optical modulation element having a sinusoidal intensity modulation pattern can be employed in order to introduce the capability to measure high-order aberrations very accurately. A sinusoidal intensity modulation produces a sinusoidal Talbot image, e.g., the carrier signal is sinusoidal. This approach results in the property that the desired aberration information can be extracted exactly through Fourier Transformation, with substantially no loss of information caused by high-order interference between the optical element diffraction pattern and the high-order aberrations. In common optical terminology, this approach eliminates "ringing" caused by sharp edge's in arbitrary non-sinusoidal intensity patterns; thus, the high-order information does not "diffract away" into high-order lobes. In principle, the sinusoidal optical element allows measurement of extremely high-order aberration information, which may be necessary to restore 20/20 vision through corrective devices.

In order to implement this approach, a good approximation to a pure sinusoidal transmission element can be employed. A suitably constructed phase modulation element could be used to produce the desired intensity modulation. For intensity modulation, the preferred transmission function comprises a continuous (grayscale) 2-dimensional sinusoidal function such shown in FIG. 7. The transmission, $\tau_I(x,y)$, of this two dimensional pattern may be described by the following equation:

$$\tau_I(x, y) = \frac{1}{2}\left(1 + \frac{1}{2}\cos\left(\frac{2\pi x}{P}\right) + \frac{1}{2}\cos\left(\frac{2\pi y}{P}\right)\right)$$

where x and y are coordinates defining position across the pattern and P corresponds to the period of the sinusoidal modulation.

Current technologies for manufacturing transmission gratings can have limited capabilities for creating grayscale transmission functions, and realizable transmission functions can be limited to binary patterns in which the transmission in a given discrete area is either 0 or 1. For this reason, a binary transmission function can be employed that preferably optimally approximates the ideal continuous sinusoidal function.

Figure 8:
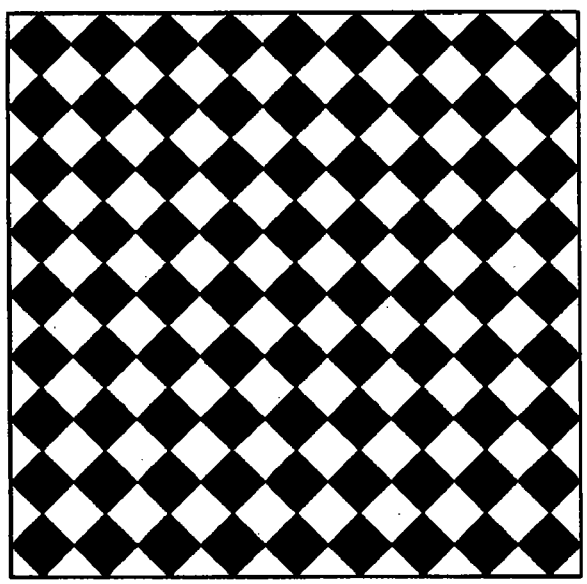
FIG. 8 is graphical illustration of a pattern resulting from the binary approximation of thresholding a continuous sinusoidal function.
Figure 8:
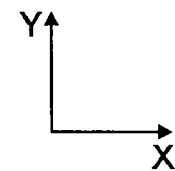
Figure 9A:
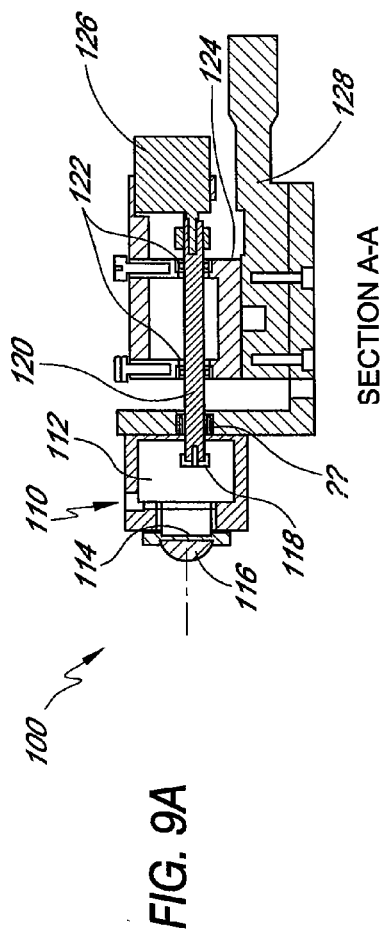
FIG. 9A is a side view of a model eye for testing wavefront sensors.
Figure 9B:
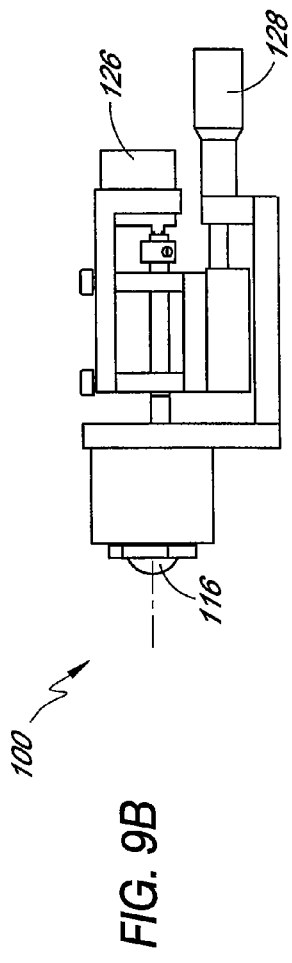
FIG. 9B is a side view of a model eye for testing wavefront sensors.
Figure 9C:
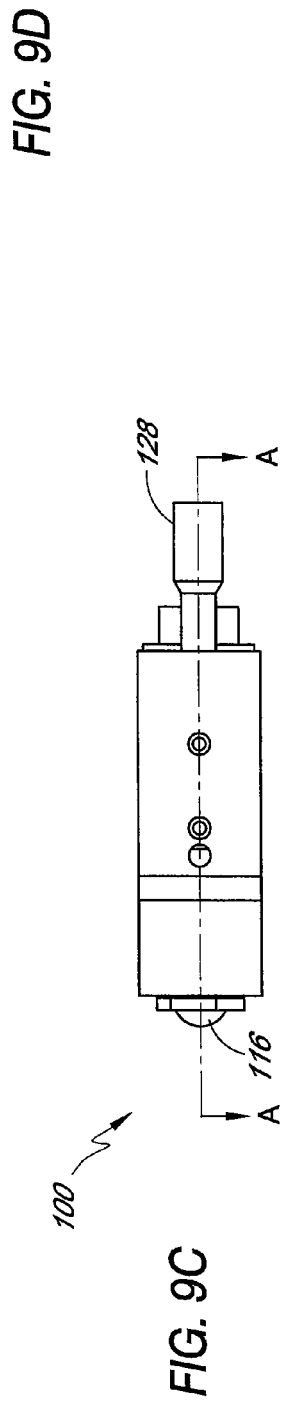
FIG. 9C is a bottom view of a model eye for testing wavefront sensors.
Figure 9D:
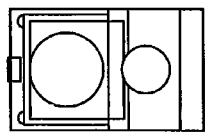
FIG. 9D is a front view of a model eye for testing wavefront sensors.

According to one embodiment, a preferred binary approximation can be obtained by thresholding the continuous sinusoidal function (rounding up/down to binary values 0 and 1) to form a pattern resembling checkerboard pattern such as a rotated checkerboard pattern (i.e., a lattice of diamond shapes) as shown in FIG. 8. The transmission, $\tau_B(x,y)$, of this two dimensional pattern may, for example, be described by the following equation:

$$\tau_B(x, y) = \text{round}\left(\frac{1}{2}\left(1 + \frac{1}{2}\cos\left(\frac{2\pi x}{P}\right) + \frac{1}{2}\cos\left(\frac{2\pi y}{P}\right)\right)\right)$$

Computer modeling was performed in which the continuous and binary periodic patterns were modulated by an aberration-free wavefront, numerically propagated to the sensor plane and analyzed for residual phase error. The residual phase error for the binary periodic patterns substantially matched that of the continuous sinusoidal periodic element, and examination of the Fourier Transforms of both periodic elements showed reduced or minimal error in the vicinity of the fundamental frequency of the periodic pattern. The periodic element advantageous because the spatial frequency spectrum is preserved in the vicinity of the fundamental spatial frequency of the ideal periodic pattern. The spectrum in the vicinity of the fundamental is not corrupted by harmonic components of the binary periodic element. The rotated checkerboard pattern is a realizable and accurate approximation to a continuous sinusoidal element and can be fabricated using inexpensive manufacturing techniques.

Other types of reticles, patterns, or periodic elements can also be used, according to various embodiments. Other methods of manufacturing sinusoidal or non-sinusoidal patterns that may or may not approximate a continuous two-dimensional sinusoidal pattern can be employed as well.

FIG. 9A-9D illustrate a "model eye" 100 that can be used to test the ophthalmic instrument 10. The model eye 100 includes an assembly 110 having a chamber 112 that can contain liquid or solution such as, for example, mineral oil. Preferably, this liquid or solution or other content in the chamber has a well-defined known index of refraction. The chamber 112 has an aperture 114 and a lens 116, for example a hard contact lens, can be, placed in front of the aperture 114 enclosing one end of the chamber. A rotating imaging disk 118 with an imaging surface is disposed in the chamber 112. The imaging disk 118 can be made from a variety of suitable materials, e.g. aluminum. The imaging disk can be flat or spherical in shape. An optical path of the model eye 100 extends from the lens 116 to the rotatable surface on the imaging disk 118, and it is along this optical path that light is provided to the model eye 100. The rotatable imaging disk 118 is disposed on a rotatable shaft 120 that can be held in place by bearings 122 in a bearing block 124. The model eye 100 can also incorporate a seal 117 to enclose the portion of the chamber 112 surrounding the rotatable shaft 120 and prevent the fluid from leaking from the chamber 112. The rotatable shaft 120 can be connected to a motor 126 that drives the shaft 120 in a rotary fashion about a longitudinal axis through the shaft. The shaft 120 in the bearing block 124 can be mounted to a micrometer stage 128 to move the shaft 120 and the rotating surface on the imaging disk 118 on the shaft so as to position the imaging disk 118 with respect to the lens 116.

In the model eye, the lens 116 corresponds to the cornea. The rotatable surface on the imaging disc 118 corresponds to the retina. The model eye 100 can be disposed in a similar location as that where a human eye 18 would be situated when the ophthalmic instrument 10 is used to perform measurements on a human eye. In particular, light from the ophthalmic instrument 10 is directed into the model eye 100 through the lens 116 and aperture 114 and reflected from within the model eye 100 back out to the ophthalmic diagnostic instrument 10. More specifically, light is propagated through the lens 116 of the model eye 100 is preferably incident on the rotatable surface of the imaging disc 118. This light is preferably reflected back out of the chamber 112 through the lens 116 and reaches the sensor 44 in the optical wavefront assembly 14 (FIG. 1A). Rotation of the imaging surface on the imaging disk 118 removes the appearance of features such as scratches in the surface of the imaging disk 118, and laser speckle, that would otherwise be imaged at the sensor 44 (FIG. 1A) and disrupt calculations used to characterize the wavefront. The rotation introduces blurring and washes out the detail of such distracting features. Fluid within the chamber 112 preferably has a known index of refraction to assist in calculations of the optical characteristics of the model eye 100. This fluid can also reduce reflections. The micrometer 128 can be adjusted to position the lens 116 and the imaging surface on the imaging disk 118 to a desired distance apart. Preferably, the micrometer 128 establishes a distance between the lens 116 and the rotating reflective surface such that a light beam propagating through the lens 116 is substantially focused down to a point formed on the rotating reflecting surface on the imaging disk 118.

The model eye 100 advantageously has a movable and rotating simulated retina back focal length. The motor 126 spins the imaging disk 118 which acts as an averaging surface for the scattering of the illumination beam. Depending on the motor speed and the integration time of the camera sensor 44, the surface can appear as a substantially lambertian source.

In various embodiments, the fluid chamber 112 can be filled with a solution which closely matches that of the eye 18. Also the lens 116 can be removed and replaced with other lenses for additional testing. Other embodiments of model eyes and methods of simulating light propagation through the eye 18 are also possible.

Figure 14:
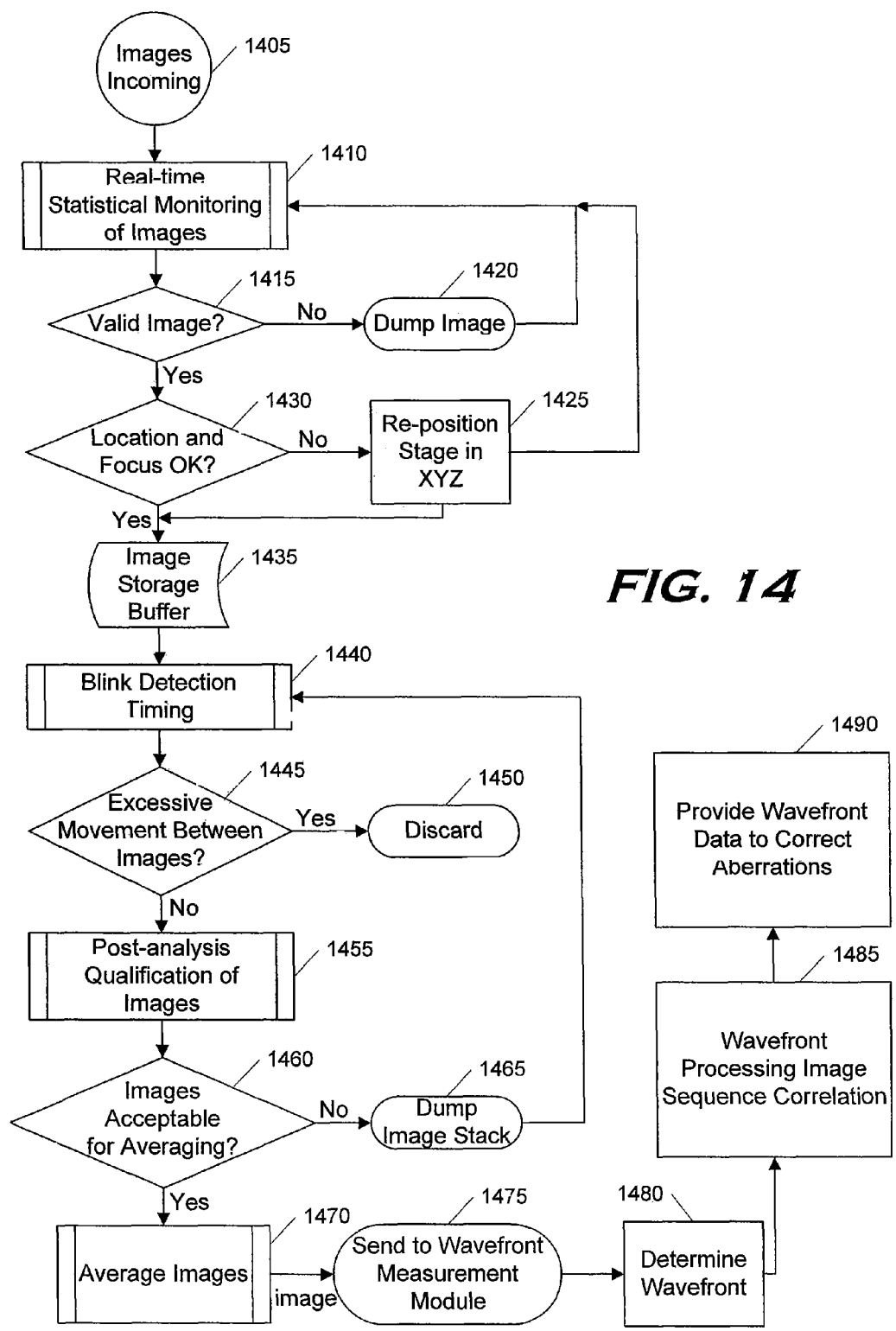
FIG. 14 is a flow diagram illustrating wavefront image processes.

In another embodiment of the invention, a process uses real-time or near real-time analysis of images created with a wavefront measuring system to identify problems in the images, provide closed loop feedback of positional information to the XYZ stage to center the pupil in the image frame, set the Z focus, and analyze captured images or sets of images to determine outliers before averaging. The flow diagram in FIG. 14 illustrates methods for monitoring images created with a wavefront measuring system such as the ophthalmic instrument 10. The methods can be implemented and used as a single method for monitoring images, or as one or more separate methods. In one embodiment, the methods for determining which images should be used for calculating a wavefront are implemented in an image monitoring module 67 in the computer 51 (FIG. 1A).

Referring to FIG. 14, at state 1405 the process receives images as input for processing. For example, the images can be provided to the computer 51 (FIG. 1A) from the wavefront sensor assembly 14 (FIG. 1A) or from another source, e.g., images stored on a computer storage medium (e.g., tape, CD, DVD, other optical disk, magnetic disk, or RAM). At state 1410, the process performs real-time or near real-time statistical monitoring of the images to determine the location of the pupil in the image, the pupil diameter, and the quality of the image. The statistical monitoring process incorporates various image processing techniques to detect erroneous results occurring from incorrect XYZ positioning of the sensor, eye movement, tear film, eye blinks, eyelashes, glint, artifacts, and spurious or uncontrolled accommodation.

In one embodiment, during statistical monitoring the process segments a wavefront image using a histogram based approach to identify the pupil from the background of the image. The process stores values that represent attributes of the image, e.g., the diameter of the pupil, the location of the pupil within the image frame, and whether the image contains a saturated spot, a bright spot or glint (undesirable image characteristics which can be detrimental to the wavefront analysis). At state 1415, the process evaluates the outcome results of state 1410 to determine whether the image is a valid or invalid image. For example, the image can be an invalid image if it contains a saturated spot, a bright return or glint, or if the image is otherwise of poor quality. If the image is invalid, the process moves to a state 1420 and discards the image from the analysis. From state 1420, the process moves to state 1410 and proceeds as described above.

After the process evaluates whether an image is valid in state 1415, the process moves to a state 1430 and checks the location of the pupil and the focus of the image. In one embodiment, the process determines the pupil location by comparing a predetermined desired pupil location in an image (usually near or at the center of the image) to the actual pupil location (e.g., the XY coordinates of the pupil determined in state 1410) of the image being evaluated. If the values representing the actual location of the pupil in the image and the desired location of the pupil in the image deviate by a predetermined amount, the process moves to a state 1425 and commands the stage 46 (FIG. 1A) to move to a new X and/or Y position so that in subsequent images the pupil will be closer to the center or in the center of the image "frame." The process creates the next image at the new location of the stage and processes the image as described herein. If the location of the pupil in the image deviates from the center of the image excessively so that the pupil is un-usable for determining a wavefront measurement (e.g., the pupil is not completely in the image), the stage is re-positioned in state 1425, the image is discarded and the process moves to state 1410 where it continues to monitor incoming images. If the location of the pupil in the image does not deviate by an amount such that the image is un-usable, the process can re-position the stage in state 1425 if necessary, the image is not discarded, and the process moves to state 1435.

In one embodiment, the process controls the focus of the image via an algorithm implemented in the image monitoring module 63 (FIG. 1A). The process controls focus by checking if a first image is in focus by determining the sharpness of the imaged pupil using various image processing techniques, e.g., analyzing high-frequency spatial components in the image. If the first image is out of focus, the process moves the Z axis of the wavefront sensor stage 46 (FIG. 2) a small amount in one direction to a new Z position. A second image is generated at the new Z position and the process analyzes this image to determine if the second image is more or less sharp. If the second image is sharper, the stage 46 continues to move in the same direction as before and subsequent images are analyzed for sharpness until the sharpness of an image passes a predetermined sharpness threshold. If the second image became less sharp or un-focused after the stage movement, the process changes the direction of the stage and the stage moves in this new direction as subsequent images are generated. The stage continues to move until the subsequent images are in focus, e.g., pass a sharpness threshold. Alternatively, two images can be generated at two Z-axis locations of the wavefront sensor stage 46, and then those images can be compared to determine which one is sharper. Following this comparison, the process generates other images while moving the stage 46 in the direction of the sharper image, until the process determines that the images pass the focus or sharpness threshold. If, after the initial stage movement, the image becomes more out of focus the stage changes direction and continues moving until the subsequent images are in focus. If the image is out of focus by a predetermined amount making the image unusable for calculating an accurate wavefront measurement, the image is discarded, and the process moves to state 1410, and proceeds as described above.

If the focus of a valid image is acceptable at state 1430, the process moves to state 1435 where one or more of the images of a pupil, e.g., a series of images, are stored in an image storage buffer, as in "image stack." The image stack can be a sequential series of images, or can be a series of images of an eye that are not sequential because of, for example, intermittent invalid images. At state 1440, the process compensates for a patient's blinking by removing images that were generated during a certain time period after the patient blinked. This compensation can improve the quality of the images used for wavefront measurements. Detecting when a patient blinks and determining the appropriate image acquisition timing to compensate for the blinks can be accomplished based on the output of the above process. In state 1440 the process performs blink detection timing to capture images from the same point in time after a blink. When a patient blinks, the image is of poor quality because the pupil is either partially or completely obscured by the eyelid and the image is thus deemed invalid by, for example, the above-described process. Wavefront images of the pupil taken too soon or too long after a blink can also be erroneous. A contributor to erroneous wavefront measurements is the eye's tear film, which typically degrades and dries out over time after a blink. If images are taken following a suitable delay period after a blink, the eye has a chance to stabilize. The delay period should not be so long that the tear film has begun to dry out or break down. During blink compensation, the process monitors the elapsed time between when the eye blinks and selects images generated after the eye has stabilized but before it dries out.

In one embodiment, a series of wavefront images is analyzed to identify an image that depicts a pupil at least partially obscured by an eyelid during a blink of the eye. This analysis may be part of the analysis conducted to determine valid images, or it may be conducted by another suitable image analysis process. The series of wavefront images is then further analyzed to identify another image that is generated after the eye has completed the blink such that this later generated image depicts a non-obscured pupil. In some embodiments, the identified image is the first image in the series of images that depicts a non-obscured pupil subsequent to the image depicting an at least partially obscured pupil. This image depicting a non-obscured pupil (e.g., a valid image), and/or valid images generated subsequent to this first image, can be stored and used for subsequent processing (e.g., determination of excessive movement between images, post-analysis qualification of images, averaging the images and determining a wavefront measurement).

In some embodiments, the process determines which images to store for further processing based on a pre-determined time interval after blinking. For example, a timer can start after the process identifies a valid image depicting a non-obscured pupil in a series of wavefront images that were taken during the blink of an eye, and one or more of the images generated subsequent to the identified image are stored to a buffer at a specific interval after the blink occurs. For example, the time interval can be, e.g., less than 0.10 seconds, or equal to or between (in seconds) 0.10-0.20, 0.20-0.30, 0.30-0.40, 0.40-0.50, 0.50-0.60, 0.60-0.70, 0.70-0.80, 0.80-0.90, 0.90-1.00, 1.00-1.10, 1.10-1.20, 1.20-1.30, 1.30-1.40, 1.40-1.50, 1.50-1.60, 1.60-1.70, 1.70-1.80, 1.80-1.90, 1.90-2.00, 2.00-2.10, 2.10-2.20, 2.20-2.30, 2.30-2.40, 2.40-2.50, 2.50-2.60, 2.60-2.70, 2.70-2.80, 2.80-2.90, 2.90-3.00, 3.00-3.10, 3.10-3.20, 3.20-3.30, 3.30-3.40, 3.04-3.50, 3.50-3.60, 3.60-170, 3.70-3.80, 3.80-3.90, 3.90-4.00, or greater than 4.00 seconds. In one preferred embodiment, the time interval is about 1.00 seconds. With this process running, a patient can look into the wavefront measurement instrument and blink normally, eliminating the possibility of capturing images during, or directly after a blink which might contaminate the data. The images identified for analysis are therefore always from about the same point in time after a blink. Images that do not meet the timing criteria can be discarded from the analysis. In an alternative embodiment, the process determines which images to store for further processing based on the number of images generated after determining that an image depicts a non-obscured pupil.

Moving to a state 1445, the process analyzes images to determine whether the movement of the pupil in successive images exceeds predetermined criteria. The pupil can move due to saccades or another eye movement. Excessive pupil movement can compromise the wavefront measurement. In one embodiment, the process determines the amount of movement of the pupil by analyzing the stored XY location of the pupil in each image of a stored stack of related images, and determines if the movement exceeds the criteria. If in state 1445 the process determines that there is excessive movement of the pupil, the process moves to a state 1450 wherein the image is discarded from the analysis and the next image in the stack of related images is analyzed. In state 1445, if the process determines that the movement of the pupil is not excessive, the image can be used for further processing, including determining a wavefront measurement of the aberrations of the eye, and the process moves to a state 1455.

At state 1455, the process stores the images that are to be used for further processing in a buffer as an image set or stack, and the images are further evaluated to determine if they should be combined to form an "average" image. The process will subsequently determine a wavefront measurement from the averaged image. Images are averaged to help remove image noise, for example, camera noise. At state 1455, the process performs further analysis of the images to determine if the images in the image set are "like" images, before they are averaged in state 1470. For example, the process can perform blob analysis to determine if the pupil is round or if there is a major inclusion in an imaged pupil, such as an eyelash or droopy eyelid. Opaque anomalies in an image such as cataracts, floaters, etc. can also be identified using image processing techniques, and these anomalies can be subsequently masked out so they do not affect forming the averaged image. Also, the identified anomalies can also be provided to the operator to alert the operator and patient to certain conditions that are present in the patient's eye. For example, the ophthalmic instrument 10 can be used for early detection of cataracts, where a cataract appears as a dark spot in the image displayed to an operator, and/or the cataract is identified by image processing software as an anomaly that requires further investigation.

Following image qualification, the process moves to a state 1460 wherein the process determines whether the stored images in a set are acceptable for averaging. If they are acceptable, the process moves to state 1470 where the images are averaged and the process provides the resulting image to the wavefront measurement module 59 (FIG. 1). In one embodiment, the images are averaged by adding together the values of like pixels (e.g., pixels corresponding to the same eye position) of each image in the image set and dividing by the number of images. If the process determines in state 1460 that the set of images is not acceptable for averaging, the process moves to state 1465 where the image stack is discarded from further processing, and then the process returns to state 1440 to process another series of images.

In state 1475 the process send the image resulting from the averaging process to the wavefront measurement module 59. At state 1480, the wavefront measurement module 59 determines a wavefront measurement using processes that are known in the art for processing Talbot images, e.g., U.S. Pat. No. 6,781,681 issued to Horwitz, titled "System and Method for Wavefront Measurement."

At state 1485, the process performs wavefront processing image sequence correlation. Here, the process compares the wavefronts from two or more average images (e.g., from two or more sets of images) to determine how similar the wavefronts are to each other and identify anomalies which were not identified in the previous processes. For example, problems relating to spurious accommodation, tear film and gaze angle can be determined by image sequence correlation. In one embodiment, wavefront processing image sequence correlation can be performed by analyzing each of the image stacks completely through the wavefront processing and comparing the wavefronts or Zernike polynomial representation. In an alternative embodiment, wavefront processing image sequence correlation can be performed on a partially processed sequence of images at any intermediate stage, such as in a Fourier space stage of processing the images. For example, wavefront data can be quickly processed to determine FFT's, and the FFT's can be compared to determine the similarity of the wavefronts. After correlating two or more wavefronts, at state 1490 the process provides the wavefront data for use to, for example, create a lens or for eye surgery to correct for the aberrations identified by the wavefront data.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A binocular wavefront measurement system configured to perform wavefront analysis on eyes of a patient, the system comprising:
   a light source configured to provide light along a source optical path to at least one of the patient's eyes;
   an optics system configured to provide an image to the first eye along a first optical path and an image to the second eye along a second optical path;
   a modulation element comprising a two-dimensional pattern, wherein the modulation element is positioned to receive light reflected from at least one of the patient's eyes; and
   a sensor system, said sensor system configurable in a first mode for performing a wavefront measurement of a first eye through a portion of the first optical path and configurable in a second mode for performing a wavefront measurement of a second eye through a portion of the second optical path, wherein the sensor system is positioned to receive at least a portion of light passing through the modulation element.

2. The system of claim 1, further comprising a stage system for positioning the sensor system to receive light from the first eye in the first mode and to receive light from the second eye in the second mode.

3. The system of claim 1, wherein the sensor system is further configured to evaluate said wavefront measurements to provide low order aberration values representing sphere, cylinder, and axis aberrations and high order aberration values representing coma, trefoil, and spherical aberrations.

4. The system of claim 1, wherein the image comprises a first image presented to the first eye and a second image presented to the second eye.

5. The system of claim 1, wherein said light source is positioned relative to the eye such that light from the light source reflected from a retina of the eye travels in a first direction and light reflected from a cornea of the eye travels in a second direction, wherein the angle of the first direction relative to the source optical path is different from the angle of the second direction relative to the source optical path such that light traveling in the second direction does not enter an optical path for receiving light in the sensor system.

6. The system of claim 5, wherein said light source further comprises one or more optical elements positioned along the source optical path so as to decrease the spot diameter of the light at the retina of the eye.

7. The system of claim 6, wherein the spot diameter of the light at the retina is less than about 1 millimeter, more preferably less than about 400 micrometers.

8. The system of claim 1, wherein said optics system comprises:
- a first internal target;
- a second internal target; and
- a path diverter with a first mode for positioning said first internal target in the first optical path and said second internal target in the second optical path, and with a second mode for positioning said first internal target out of the first optical path and said second internal target out of the second optical path, wherein said first and second optical paths extend to a location external to the binocular wavefront system when said optical path diverter is positioned in the first mode.

9. The system of claim 8, wherein said first and second internal targets are a stereoscopic image pair.

10. The system of claim 8, wherein the position of said first internal target and said second internal target is adjustable so as to stimulate an eye accommodation when viewing said first internal target and said second internal target through the optics system.

11. The system of claim 1, wherein the optics system comprises a convergence device located so as to provide an image from at least one of the first optical and second optical paths to at least one of the first and second eyes so as to invoke a convergence accommodation state of the eyes.

12. The system of claim 11, wherein the convergence device comprises at least one low-angle prism.

13. The system of claim 1, wherein said optics system comprises:
- a first set of optical elements configurable for controlling aberrations in a first eye; and
- a second set of optical elements configurable for controlling aberrations in a second eye.

14. The system of claim 13, wherein the aberrations comprise spherical, astigmatism or coma.

15. The system of claim 13, wherein said optics system comprises at least one adaptive optics mirror having a movable mirror surface, said at least one adaptive optics mirror positioned in one of the first and second optical paths, and said at least one adaptive optics mirror being configurable for correcting an aberration by adjusting the movable mirror surface.

16. The system of claim 1, wherein said optics system further comprises a target light system for illuminating internal targets.

17. The system of claim 16, wherein the target light system is controllably variable to control the intensity of the illumination to provides illumination simulating different lighting conditions, wherein the different lighting conditions are selected from the group consisting of daylight, tungsten, fluorescent, moonlight, and night driving.

18. The binocular wavefront measurement system of claim 17, further comprising a computer connected to the sensor system and the target light system, said computer configured to determine the diameter of a pupil of an eye and to control the intensity of the illumination of the light source based on the diameter of the pupil.

19. The system of claim 1, wherein said sensor system comprises:
- a light source for emitting a light beam along a source optical path;
- an obstruction element having a blocking portion, said obstruction element disposed so as to position said blocking portion in the source optical path to obstruct a center portion of the light beam and produce an annular-shaped light beam for illuminating the retina of an eye;
- a modulation pattern element positioned in a path of a light beam reflected from the eye; and
- a sensor positioned to receive at least a portion of the light passing through said modulation pattern element so as to detect a wavefront aberration of the eye.

20. The system of claim 19, wherein said light source provides a collimated light beam having a beam diameter of about 2-3 mm in diameter, and wherein the blocking portion of said obstruction element is about 1.5 to 2.5 mm in diameter.

21. The system of claim 1 wherein the modulation element comprises a two-dimensional sinusoidal pattern.

22. The system of claim 1 wherein the modulation element comprises a two-dimensional checkerboard pattern.

* * * * *